(12) United States Patent
Rabbitts et al.

(10) Patent No.: US 11,970,469 B2
(45) Date of Patent: Apr. 30, 2024

(54) COMPOUNDS USEFUL IN THE TREATMENT OF DISORDERS ASSOCIATED WITH MUTANT RAS

(71) Applicant: Oxford University Innovation Limited, Oxford (GB)

(72) Inventors: Terrence Rabbitts, Headington (GB); Camilo Quevedo, Headington (GB); Carole Bataille, Oxford (GB)

(73) Assignee: THE INSTITUTE OF CANCER RESEARCH: ROYAL CANCER HOSPITAL, London (GB)

( * ) Notice: Subject to any disclaimer, the term of this patent is extended or adjusted under 35 U.S.C. 154(b) by 19 days.

(21) Appl. No.: 15/734,244

(22) PCT Filed: Jun. 3, 2019

(86) PCT No.: PCT/GB2019/051536
§ 371 (c)(1),
(2) Date: Dec. 2, 2020

(87) PCT Pub. No.: WO2019/234405
PCT Pub. Date: Dec. 12, 2019

(65) Prior Publication Data
US 2021/0214322 A1  Jul. 15, 2021

(30) Foreign Application Priority Data
Jun. 4, 2018  (GB) ..................................... 1809102

(51) Int. Cl.
| | | |
|---|---|---|
| C07D 265/30 | (2006.01) | |
| A61K 45/06 | (2006.01) | |
| C07C 217/92 | (2006.01) | |
| C07C 237/30 | (2006.01) | |
| C07D 213/74 | (2006.01) | |

(52) U.S. Cl.
CPC ............ *C07D 265/30* (2013.01); *A61K 45/06* (2013.01); *C07C 217/92* (2013.01); *C07C 237/30* (2013.01); *C07D 213/74* (2013.01)

(58) Field of Classification Search
None
See application file for complete search history.

(56) References Cited

U.S. PATENT DOCUMENTS

| | | |
|---|---|---|
| 5,739,169 A | 4/1998 | Ocain et al. |
| 9,687,491 B1 | 6/2017 | Rabizadeh et al. |

FOREIGN PATENT DOCUMENTS

| | | | |
|---|---|---|---|
| EP | 2 418 209 A1 | 2/2012 | |
| WO | 2004/048314 A1 | 6/2004 | |
| WO | 2005/012262 A1 | 2/2005 | |
| WO | WO 2005/012262 * | 2/2005 | .......... C07D 239/42 |
| WO | 2007/056151 A2 | 5/2007 | |
| WO | 2010/080474 A1 | 7/2010 | |
| WO | 2010/083975 A1 | 7/2010 | |
| WO | 2011/157397 A1 | 12/2011 | |
| WO | 2012/052179 A1 | 4/2012 | |
| WO | 2012/126922 A1 | 9/2012 | |
| WO | 02/11724 A2 | 2/2020 | |

OTHER PUBLICATIONS

CAS RN 17313-40-5 (entered into STN on Nov. 16, 1984) (Year: 1984).*
CAS RN 1235467-43-2 (entered into STN on Aug. 6, 2010) (Year: 2010).*
Anderson (Chem and Biol 10:787-797, 2003) (Year: 2003).*
Thiel (Nature Biotechnol 2:513-519, 2004) (Year: 2004).*
CAS RN 702641-99-4 (entered into STN on Jul. 2, 2004) (Year: 2004).*
CAS RN 1119086-11-1 (entered into STN on Mar. 11, 2009) (Year: 2009).*
International Search Report & Written Opinion for WO2019/234405 (PCT/GB2019/051536), dated Jul. 23, 2019, pp. 1-22.
UK Search Report for GB1809102.5, dated Jan. 29, 2019, pp. 1-5.
Abimael Cruz-Migoni et al: "Structure-based development of new RAS-effector inhibitors from a combination of active and inactive RAS-binding compounds", PNAS, vol. 116, No. 7, Jan. 25, 2019 (Jan. 25, 2019), pp. 2545-2550.
Howard Jong et al: "One-Pot Palladium-Catalyzed Cross-Coupling Treble of Borylation, the Suzuki Reaction and Amination", Advanced Synthesis & Catalysis, vol. 359, No. 4, Jan. 26, 2017 (Jan. 26, 2017), pp. 616-622.
M. P. Patricelli et al: "Selective Inhibition of Oncogenic KRAS Output with Small Molecules Targeting the Inactive State", Cancer Discovery, vol. 6, No. 3, Mar. 1, 2016 (Mar. 1, 2016), pp. 316-329.
Organic Letters, vol. 14, No. 21, 2012, pp. 5578-5581, GROB et al. "One-pot C—N/C—C cross-coupling of methyliminodiacetic acid boronyl arenes enabled by protective enolization".

(Continued)

*Primary Examiner* — Craig D Ricci
(74) *Attorney, Agent, or Firm* — Thomas |Horstemeyer, LLP

(57) ABSTRACT

The present invention relates to compounds of Formula I as defined herein, and salts and solvates thereof. (I) The present invention also relates to pharmaceutical compositions comprising compounds of Formula (I), and to compounds of Formula (I) for use in the treatment of proliferative disorders, such as cancer, as well as other diseases or conditions in which inhibition of a RAS-effector protein-protein interaction is implicated.

10 Claims, 1 Drawing Sheet

(56) References Cited

OTHER PUBLICATIONS

Qi Sun et al: "Discovery of Small Molecules that Bind to K-Ras and Inhibit Sos-Mediated Activation", Angewandte Chemie, International Edition, vol. 51, No. 25, Jun. 18, 2012 (Jun. 18, 2012), pp. 6140-6143.
Welsch Matthew E. et al: "Multivalent Small-Molecule Pan-RAS Inhibitors", Cell, Elsevier, Amsterdam, NL, vol. 168, No. 5, Feb. 27, 2017 (Feb. 27, 2017), p. 878.
European Office Action for Application No. 19 730 487.6, dated Dec. 14, 2021, pp. 1-5.
Grob et al., Org Lett., 2012, vol. 14, No. 21, 5578-5581, "This is a chemical synthesis paper relating to cross-coupling bf boronyl arenes".
International Preliminary Report on Patentability for WO2019/234405 (PCT/GB2019/051536), dated Dec. 8, 2020, pp. 1-10.

* cited by examiner

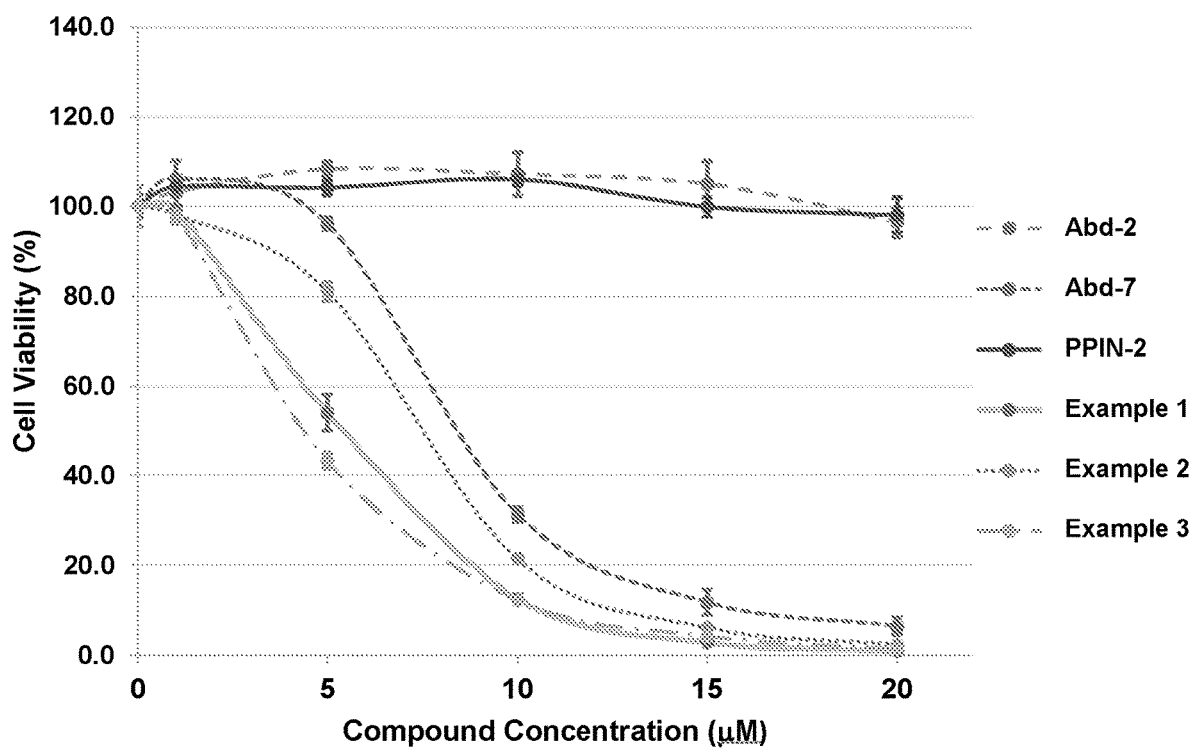

ND STAGE OF INTERNATIONAL...

COMPOUNDS USEFUL IN THE TREATMENT OF DISORDERS ASSOCIATED WITH MUTANT RAS

CROSS-REFERENCE TO RELATED APPLICATIONS

This application is the National Stage of International Application No. PCT/GB2019/051536, filed Jun. 3, 2019, which claims priority to GB 1809102.5, filed Jun. 4, 2018, which are entirely incorporated herein by reference.

INTRODUCTION

This application relates to compounds of Formula I as defined herein and salts or solvates thereof.

The compounds of Formula I and their salts have the capability to inhibit protein-protein interactions, in particular interactions between RAS and effector proteins (such as RAF and PI3K) and may be used to treat diseases or conditions mediated, at least in part, by mutant RAS, such as cancer.

The present application further provides pharmaceutical compositions comprising a compound of Formula I, or a pharmaceutically acceptable salt or solvate thereof, and an pharmaceutically acceptable excipient.

The present application also provides methods of treating a proliferative disorder, such as cancer, in a subject in need thereof comprising administering to the subject a compound of Formula I or a pharmaceutically acceptable salt or solvate thereof.

BACKGROUND OF THE INVENTION

The aetiology of many human diseases such as cancer, neural degeneration and inflammation involves abnormal proteins participating in macromolecular complexes to elicit a biologically relevant effect. As such, protein-protein interactions represent a major potential drug target for manifold human disease indications.

The RAS proteins are guanine nucleotide binding molecules that play key roles in signal transduction as molecular switches, mediated through two switch regions displaying conformational differences between active (GTP bound) and inactive (GDP bound) states (Vetter and Wittinghofer, 2001). Most of the RAS effectors bind to these RAS switch regions (Downward, 2003). RAS is the most important target in cell transformation, being involved in cell proliferation and differentiation through the RAF-MEK-ERK cascade (Marshall, 1995; Kolch, 2005) and cell survival through activation of PI3K (Downward, 2003). The RAS effector, RAL-GDS, is also involved in RAS-dependent tumorigenesis in vivo (Gonzalez-Garcia et al, 2005) and cell transformation in human cells (Rangarajan et al, 2004).

Activating RAS gene mutations are found in as many as 30% of humans, with the highest frequencies in pancreas, colon and lung adenocarcinoma. Mutations of the RAS proteins (K, H or NRAS) create constitutively activated GTP-bound forms that promote cell transformation in a signal-independent manner (Adjei, 2001). In addition, secondary RAS-associated aberrations such as mutation or overexpression of receptor tyrosine kinases (e.g. EGFR, ERBB2) have been indicated in many cancers that lack RAS mutation (Mendelsohn and Baselga, 2000).

Thus, inhibiting aberrant RAS function has been an exciting possible mode of human cancer therapy. This notion has been supported by observations in mouse models in which oncogenic RAS has been shown to be essential for early onset of tumours and necessary for maintenance of tumour viability (Johnson et al, 2001), as tumours harbouring mutant RAS can regress when mutant RAS expression is stopped (Chin et al, 1999; Fisher et al, 2001).

These facts highlight activated RAS proteins as attractive targets for cancer therapy. Despite this, anti-RAS therapies have not yet been particularly effective (Friday and Adjei, 2005). Farnesyltransferase inhibitors (FTIs) can inhibit membrane localisation of RAS proteins by preventing post-translational modification, and thus blocking downstream RAS signalling. However, the antitumour activity of FTIs may only partly be due to targeting RAS and may also affect farnesylation of other proteins (Friday and Adjei, 2005).

An ideal RAS-based anticancer therapy would involve reagents that can specifically inhibit oncogenic RAS. Antibodies have such qualities of specificity and affinity that can easily be manipulated. However, most oncogenic proteins, including RAS, are located inside cells and not available for antibody-mediated targeting.

Over the last decade, antibody engineering has led to development of fragments that can be expressed intracellularly (intrabodies) (Cattaneo and Biocca, 1997), but there are still few intrabodies that work efficiently in the reducing environment of cells due to the usual need for disulphide bonds for correct folding. To overcome this limitation, intracellular antibody capture (IAC) has been developed, based on in vivo yeast two-hybrid screening (Visintin et al, 1999; Tse et al, 2002; Tanaka and Rabbitts, 2003), and it has been shown that single variable region (V) domains (iDabs) are highly efficient as intrabodies (Tanaka et al, 2003).

A single domain VH intrabody binding specifically to activated GTP-bound RAS with high affinity has been shown to neutralise oncogenicity in cancerous cells harbouring a RAS mutation (Tanaka et al, 2007). The crystal structure of the intrabody bound to mutant RAS, solved to 2 Å, shows that the intrabody specifically recognises the conformational structure of oncogenic RAS and inhibits RAS-effector protein interactions with RAS.

Nonetheless, there are currently few small-molecule drugs in clinical trials that are capable of impeding protein interactions, since these generally require clefts in a protein into which a small molecule can fit (Blundell et al, 2006).

There is a need in the art for the development of novel approaches to target protein-protein interactions. In particular, there is a need in the art for the provision of molecules capable of penetrating cells and which can bind to RAS and inhibit protein-protein interactions, in particular aberrant RAS-effector interactions, with high affinity and/or specificity. Such molecules represent promising treatments for proliferative disorders such as cancer.

SUMMARY OF THE INVENTION

In one aspect, the present invention provides a compound as defined herein, and/or a salt or solvate thereof.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer.

In another aspect, the present invention provides a compound as defined herein, or a pharmaceutically acceptable salt or solvate thereof, or a pharmaceutical composition as defined herein, for use in inhibiting a RAS-effector protein-protein interaction.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer.

In another aspect, the present invention provides the use of a compound as defined herein, or a pharmaceutically acceptable salt or solvate thereof, in the manufacture of a medicament for use in inhibiting a RAS-effector protein-protein interaction.

In another aspect, the present invention provides a method of inhibiting a RAS-effector protein-protein interaction in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a combination comprising a compound, or a pharmaceutically acceptable salt or solvate thereof, as defined herein, with one or more additional therapeutic agents.

Preferred, suitable, and optional features of any one particular aspect of the present invention are also preferred, suitable, and optional features of any other aspect.

BRIEF DESCRIPTION OF THE FIGURES

FIG. 1 shows the effect of compounds of the invention and various reference compounds on DLD-1 cells at 72 hours at concentrations of 5, 10, 15 and 20 µM.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I" refer to and include any and all compounds described by and/or with reference to Formula I unless specifically stated otherwise. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, either by themselves or in combination with additional agents. The various hydrocarbon-containing moieties provided herein may be described using a prefix designating the minimum and maximum number of carbon atoms in the moiety, e.g. "$(C_a-C_b)$". For example, $(C_a-C_b)$alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene (—$CH_2$—), the ethylene isomers (—$CH(CH_3)$— and —$CH_2CH_2$—), the propylene isomers (—$CH(CH_3)CH_2$—, —$CH(CH_2CH_3)$—, —$C(CH_3)_2$—, and —$CH_2CH_2CH_2$—), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl.

As used herein by themselves or in conjunction with another term or terms, "arylene" and "arylene group" refer to a phenylene ($-C_6H_4-$) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2-$). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydronaphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2-$). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, $-CF_3$, $-CHF_2$, $-CH_2F$, $-CF_2CF_3$, $-CH_2CF_3$, $-CH_2CF_3$, $-CF_2CH_3$, $-CH_2CF_3$, $-CF_2CF_2CF_3$, $-CF_2CH_2CH_3$, $-CF=CF_2$, $-CCl=CH_2$, $-CBr=CH_2$, $-CI=CH_2$, $-C\equiv C\equiv CF_3$, $-CHFCH_2CH_3$ and $-CHFCH_2CF_3$. Haloalkyl groups can be substituted or unsubstituted.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin- 2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein, the term "azine" refers to a 6-membered heterocyclic ring which is derived from a phenyl ring in which one or more ring methine (CH) groups have been replaced by a nitrogen atom. Examples of azines include mono nitrogen groups such as pyridines; di-nitrogen (diazine) groups such as pyridazines, pyrimidines and pyrazines; and tri-nitrogen species (triazines) such as 1,2,3-triazine, 1,24-triaiznes and 1,3,5-triazines.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Suitably, an alkyl heteroaryl group comprises is a 5- or 6-membered heteroaryl ring comprising one, two or three heteroatoms selected from N, O or S and a alkyl moiety selected from methyl, ethyl or propyl.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-2-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2-$). Alkylheteroycloalkyl groups can be substituted or unsubstituted.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—$CH_3$), it can be optionally substituted by 1 to 3 $R^5$.

As used herein by themselves or in conjunction with another term or terms, "subject(s)" and "patient(s)", refer to animals (e.g. mammals), particularly humans. Suitably, the "subject(s)" and "patient(s)" may be a non-human animal (e.g. livestock and domestic pets) or a human.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

As used herein, the term direct bond means that the two adjacent groups (e.g. in the case of $J^{1a}$, $(CR^eR^f)_a$ and $(CR^gR^h)_b$) are directly linked, (i.e. $(CR^eR^f)_a$—$(CR^gR^h)_b$).

As used herein, the term "RAS-effector protein-protein interaction" refers to the interaction between RAS and a RAS effector.

As used herein, the term "RAS effector" refers to proteins which interact with the active GTP-bound form of RAS in order to transmit signals for cell proliferation and differentiation. In one embodiment, the RAS effectors are protein kinases, lipid kinases and guanine nucleotide exchange factors. Suitably, the RAS effectors are protein kinases. In one embodiment, the RAS effectors are selected from PLCε (epsilon), PKCζ (zeta), PI3K, RASSF, RAF, RalGEF, RIN, AF-6, GAP and TIAM1, suitably selected from PI3K, RAF and RalGEF.

Compounds

Aspects and embodiments of the compounds of the present invention are further defined in the numbered paragraphs which follow:

1. A compound of Formula I, or a salt or solvate thereof:

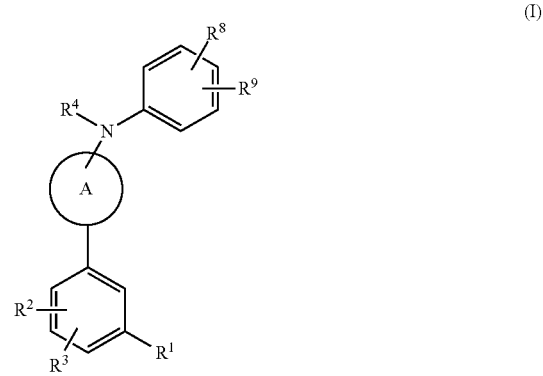

(I)

wherein,

A is selected from a phenyl or azine ring, each of which may be optionally substituted by one or more group selected from hydrogen, hydroxyl, =O, halogen, CN, $C_{1-6}$ haloalkyl, $C_{1-6}$ haloalkoxy, O—$C_{1-6}$ alkyl, $C_{1-6}$ alkyl and $NR^pR^q$, wherein $R^p$ and $R^q$ are independently selected from hydrogen, $C_{1-6}$ alkyl and $C(O)C_{1-3}$alkyl;

$R^1$ is selected from $C_{1-6}$ alkoxy and $NR^pR^q$;

$R^2$ and $R^3$ are independently selected from the group consisting of hydrogen, hydroxyl, halogen, CN, $C_{1-6}$ haloalkyl, $C_{1-6}$ haloalkoxy, O—$C_{1-6}$alkyl and $C_{1-6}$alkyl;

$R^4$ is selected from hydrogen and alkyl;

R[8] is selected from selected from the group consisting of hydrogen, hydroxyl, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)R[d], —C(=O)OR[d], —C(=O)NR[c]R[d], —C(O)C(=O)R[d], —NR[c]R[d], —NR[c]C(=O)R[d], —NR[c]C(=O)OR[d], —NR[c]C(=O)NR[c]R[d], —NR[c]S(=O)₂R[d], —NR[c]S(=O)₂NR[c]R[d], —OR[d], —SR[d], —OC(=O)R[d], —OC(=O)NR[c]R[d], —OC(=O)OR[d], —S(=O)₂R[d], —S(=O)R[d], —OS(=O)R[d], —OS(=O)₂R[d], —OS(=O)₂OR[d], —S(=O)NR[c]R[d], —OS(=O)₂NR[c]R[d] and —S(=O)₂NR[c]R[d];

R[9] is selected from the group consisting of hydroxyl, halogen, CN, $C_{1-6}$ haloalkyl, $C_{1-6}$ haloalkoxy, $C_{1-6}$alkyl, O—$C_{1-6}$alkyl, $C_{3-6}$cycloalkyl, 3-10 membered heterocycloalkyl, —C(=O)R[d], —C(=O)OR[d], —C(=O)NR[c]R[d], —C(O)C(=O)R[d], —NR[c]R[d], —NR[c]C(=O)R[d], —NR[c]C(=O)OR[d], —NR[c]C(=O)NR[c]R[d], —NR[c]S(=O)₂R[d], —NR[c]S(=O)₂NR[c]R[d], —OR[d], —SR[d], —OC(=O)R[d], —OC(=O)NR[c]R[d], —OC(=O)OR[d], —S(=O)₂R[d], —S(=O)R[d], —OS(=O)R[d], —OS(=O)₂R[d], —OS(=O)₂OR[d], —S(=O)NR[c]R[d], —OS(=O)₂NR[c]R[d] and -and S(=O)₂NR[c]R[d]; wherein said $C_{3-6}$ cycloalkyl, $C_{1-6}$ alkyl, and 3-10 membered heterocycloalkyl are optionally substituted with one or more groups selected from hydroxyl, halogen, =O, CN, HNMe, NMe₂, $C_{1-6}$ haloalkyl, $C_{1-6}$ haloalkoxy, $C_{3-6}$ cycloalkyl, $C_{1-6}$ alkyl, and O—$C_{1-6}$ alkyl; or R[9] is a group of Formula II:

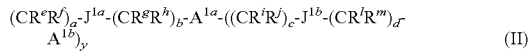

(II)

wherein,

R[e], R[f], R[g], R[h], R[i], R[j], R[l], R[m] are independently selected from hydrogen and $C_{1-6}$ alkyl;

$a$, $b$, $c$ and $d$ are independently selected from 0, 1, 2, 3 and 4, and $y$ is selected from 0 and 1;

J[1a] is selected from the group consisting of a direct bond, O, S, CH₂, C(O), C(O)NR[s1], NR[s1]C(O), NR[s1]C(O)NR[s1], NR[s1]C(O)O, OC(O)NR[s1] and NR[s1]; where R[s1] is selected from hydrogen and $C_{1-6}$ alkyl;

J[1b] is selected from the group consisting of a direct bond, O, S, CH₂, C(O), C(O)NR[s1], NR[s1]C(O), NR[s1]C(O)NR[s1], NR[s1]C(O)O, OC(O)NR[s1] and NR[s1]; where R[s1] is selected from hydrogen and $C_{1-6}$ alkyl;

A[1a] is selected from the group consisting of $C_{3-11}$ cycloalkyl optionally substituted by one or more R[k], $C_{6-11}$ aryl optionally substituted by one or more R[k], 3-15 membered heterocycloalkyl optionally substituted by one or more R[k], 5-15 membered heteroaryl optionally substituted by one or more R[k]; and A[1b] is selected from the group consisting of $C_{3-11}$ cycloalkyl optionally substituted by one or more R[r], $C_{6-11}$ aryl optionally substituted by one or more R[r], 3-15 membered heterocycloalkyl optionally substituted by one or more R[r], 5-15 membered heteroaryl optionally substituted by one or more R[r]; and R[k] and R[r] are independently selected from the group consisting of hydrogen, hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, phenyl, benzyl, alkylheterocycloalkyl, alkylheteroaryl, —C(=O)R[d], —C(=O)OR[d], —C(=O)NR[c]R[d], —C(O)C(=O)R[d], —NR[c]R[d], —NR[c]C(=O)R[d], —NR[c]C(=O)OR[d], —NR[c]C(=O)NR[c]R[d], —NR[c]S(=O)₂R[d], —NR[c]S(=O)₂NR[c]R[d], —OR[d], —SR[d], —OC(=O)R[d], —OC(=O)NR[c]R[d], —OC(=O)OR[d], —S(=O)₂R[d], —S(=O)R[d], —OS(=O)R[d], —OS(=O)₂R[d], —OS(=O)₂OR[d], —S(=O)NR[c]R[d], —OS(=O)₂NR[c]R[d], —S(=O)₂NR[c]R[d]; where said $C_{3-6}$ cycloalkyl, $C_{1-6}$ alkyl, 3-10 membered heterocycloalkyl, phenyl, benzyl, alkylheterocycloalkyl, alkylheteroaryl, and O—$C_{1-6}$alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, NR[c]R[d], $C_{1-6}$ alkyl, O—$C_{1-6}$ alkyl, and phenyl; and each R[c] is independently selected from the group consisting of hydrogen, hydroxyl, halogen, CN, $C_{1-6}$ haloalkyl, $C_{3-6}$ cycloalkyl, $C_{1-6}$ alkyl and O—$C_{1-6}$ alkyl;

each R[d] is independently selected from the group consisting of hydrogen, hydroxyl, halogen, CN, $C_{1-6}$ haloalkyl, 3-10 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, O—$C_{1-6}$ alkyl, $C_{6-11}$ aryl, 3-10 membered heterocycloalkyl and $C_{3-6}$ cycloalkyl are optionally substituted with one or more groups selected from hydroxyl, =O, halogen, CN, NH₂, NHMe, NMe₂, ($C_{1-6}$ haloalkyl, $C_{3-6}$ cycloalkyl, $C_{6-11}$ aryl, $C_{1-6}$ alkyl and O—$C_{1-6}$ alkyl; or R[c] and R[d], when attached to the same atom, together with the atom to which they are attached form a 3-10 membered ring, optionally containing one or more for heteroatoms selected from O, NH and S, and wherein said ring is optionally substituted with one or more R[a], wherein R[a] is selected from the group consisting of hydroxyl, halogen, $C_{1-6}$ alkyl, CN, $C_{1-6}$ haloalkyl, $C_{1-6}$ haloalkoxy, $C_{3-6}$ cycloalkyl, 3-10 membered heterocycloalkyl, wherein said $C_{1-6}$ alkyl, $C_{3-6}$ cycloalkyl and 3-10 membered heterocycloalkyl are optionally substituted with one or more groups selected from hydroxyl, halogen, CN, NHMe, NMe₂, NH₂, $C_{1-6}$ haloalkyl, $C_{3-6}$ cycloalkyl, $C_{1-6}$ alkyl and O—$C_{1-6}$ alkyl 2. A compound of formula I, or a salt or solvate, thereof according to paragraph 1 wherein A is selected from the group consisting of phenyl, pyridinyl, pyridazinyl, pyrimidinyl and pyrazinyl.

3. A compound of formula I, or a salt or solvate, according to any preceding paragraph wherein A is selected from phenyl and pyridinyl.

4. A compound of formula I, or a salt or solvate, according to paragraph 1 selected from a compound of subformula Ia, Ib, Ic and Id, or a salt or solvate:

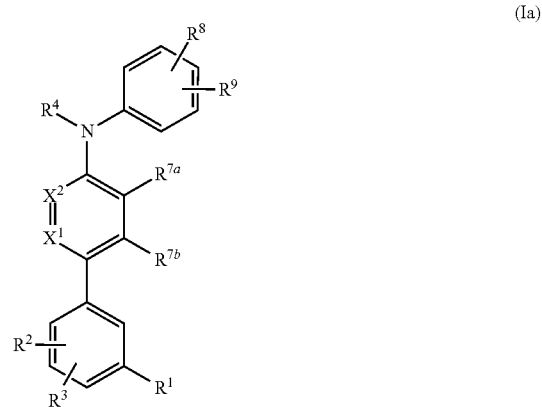

(Ia)

-continued

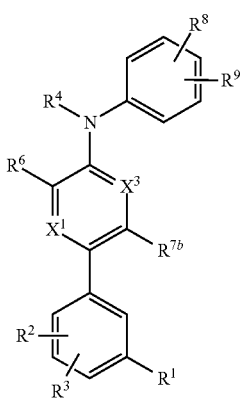

(Ib)

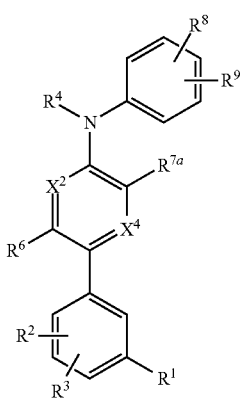

(Ic)

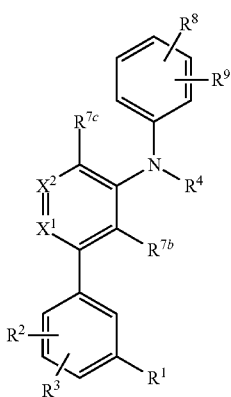

(Id)

wherein $X^1$, $X^2$, $X^3$ and $X^4$ are independently selected from N and $CR^5$;

$R^5$ and $R^6$ are independently selected from the group consisting of hydrogen, hydroxyl, =O, halogen, CN, $C_{1-6}$haloalkyl, $C_{1-6}$haloalkoxy, O—$C_{1-6}$alkyl, $C_{1-6}$alkyl and $NR^pR^q$;

Each $R^{7a}$, $R^{7b}$ and $R^{7c}$ are independently selected from the group consisting of hydrogen, hydroxyl, halogen, CN, $C_{1-6}$haloalkyl, $C_{1-6}$haloalkoxy, O—$C_{1-6}$ alkyl and $C_{1-6}$ alkyl; and $R^1$, $R^2$, $R^3$, $R^4$, $R^8$ and $R^9$ are as defined in paragraph 1.

5. A compound of formula Ia, or a salt or solvate, according to paragraph 4 wherein:

(i) $X^1$ is N; or
(ii) $X^2$ is N; or
(iii) $X^1$ and $X^2$ is N; or
(iv) $X^1$ and $X^2$ are $CR^5$.

6. A compound of formula Ib, or a salt or solvate, according to paragraph 4 wherein:

(i) $X^1$ is N; or
(ii) $X^3$ is N; or
(iii) $X^1$ and $X^3$ are N; or
(iv) $X^1$ and $X^3$ are $CR^5$.

7. A compound of formula Ic, or a salt or solvate, according to paragraph 4 wherein:

(i) $X^1$ is N; or
(ii) $X^4$ is N; or
(iii) $X^1$ and $X^4$ are N; or
(iv) $X^1$ and $X^4$ are $CR^5$.

8. A compound of formula Id, or a salt or solvate, according to paragraph 4 wherein:

(i) $X^1$ is N; or
(ii) $X^2$ is N; or
(iii) $X^1$ and $X^2$ are N; or
(iv) $X^1$ and $X^2$ are $CR^5$.

9. A compound of formula I, or a salt or solvate, according to any one of paragraphs 1 and 4 selected from a compound of sub-formula Ie, If and Ig or a salt or solvate:

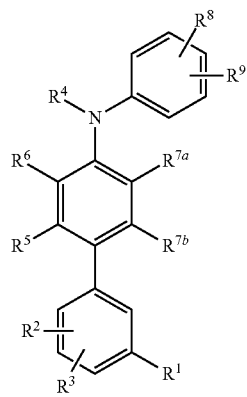

(Ie)

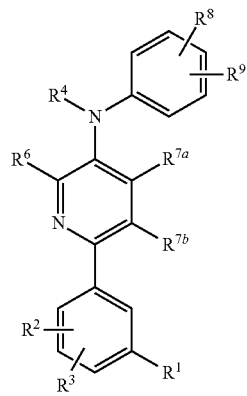

(If)

15
-continued

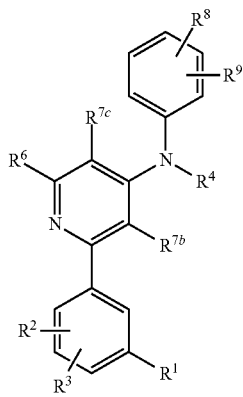
(Ig)

wherein $R^5$ and $R^6$ are independently selected from hydrogen, hydroxyl, =O, halogen, CN, $C_{1-6}$ haloalkyl, $C_{1-6}$haloalkoxy, O—$C_{1-6}$alkyl, $C_{1-6}$alkyl and $NR^pR^q$;

$R^{7a}$, $R^{7b}$ and $R^{7c}$ are independently selected from hydrogen, hydroxyl, halogen, CN, $C_{1-6}$ haloalkyl, $C_{1-6}$haloalkoxy, O—$C_{1-6}$ alkyl and $C_{1-6}$ alkyl; and $R^1$, $R^2$, $R^3$, $R^4$, $R^8$ and $R^9$ are as defined in paragraph 1.

10. A compound of formula I, or a salt or solvate, according to any one of paragraphs 1 and 4 selected from a compound of sub-formula Ie or a salt or solvate.

11. A compound of formula I, or a salt or solvate, according to any one of paragraphs 1 and 4 selected from a compound of sub-formula If or a salt or solvate.

12. A compound of formula I, or a salt or solvate, according to any one of paragraphs 1 and 4 selected from a compound of sub-formula Ih, Ii, Ij and Ik or a salt or solvate:

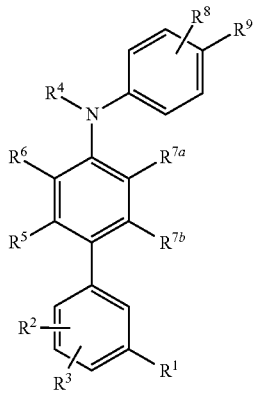
(Ih)

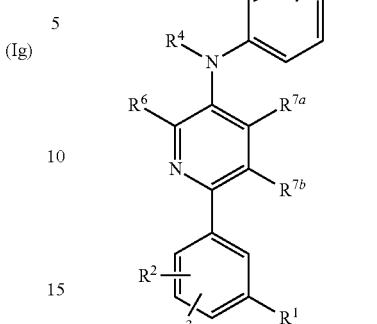
(Ii)

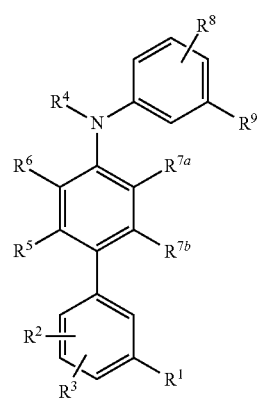
(Ij)

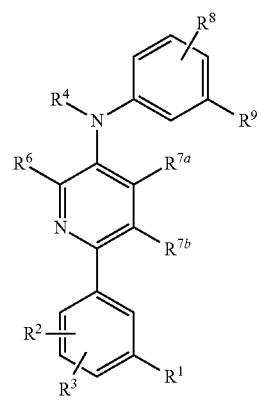
(Ik)

13. A compound according to formula I, or a salt or solvate thereof, according to any one of the preceding paragraphs wherein $R^1$ is selected from $C_{1-3}$ alkoxy and $NR^pR^q$.

14. A compound according to formula I, or a salt or solvate thereof, according to any one of the preceding paragraphs wherein $R^1$ is selected from $C_{1-3}$alkoxy, $NH_2$, NHMe, and $NMe_2$.

15. A compound according to formula I, or a salt or solvate thereof, according to any one of the preceding paragraphs wherein $R^1$ is OMe.

16. A compound according to formula I, or a salt or solvate thereof, according to any one of the preceding paragraphs wherein $R^2$ and $R^3$ are independently selected from the group consisting of hydrogen, hydroxyl, halogen, $C_{1-6}$haloalkyl, $C_{1-6}$haloalkoxy, O—$C_{1-6}$ alkyl and $C_{1-6}$ alkyl.

17. A compound according to formula I, or a salt or solvate thereof, according to any one of the preceding paragraphs wherein $R^2$ and $R^3$ are independently selected from the group consisting of hydrogen, hydroxyl, halogen, O—$C_{1-6}$ alkyl and $C_{1-6}$ alkyl.

18. A compound according to formula I, or a salt or solvate thereof, according to any one of the preceding paragraphs wherein $R^2$ and $R^3$ are independently selected from hydrogen, halogen and $C_{1-6}$ alkyl.

19. A compound according to formula I, or a salt or solvate thereof, according to any one of the preceding paragraphs wherein $R^5$ is selected from the group consisting of hydrogen, hydroxyl, halogen, $C_{1-6}$haloalkyl, $C_{1-6}$haloalkoxy, O—$C_{1-6}$ alkyl, $C_{1-6}$ alkyl and $NR^pR^q$.

20. A compound according to formula I, or a salt or solvate thereof, according to any one of the preceding paragraphs wherein $R^5$ is selected from the group consisting of hydrogen, hydroxyl, halogen, O—$C_{1-6}$ alkyl, $C_{1-6}$ alkyl and $NR^pR^q$.

21. A compound according to formula I, or a salt or solvate thereof, according to any one of the preceding paragraphs wherein $R^5$ is selected from the group consisting of hydrogen, hydroxyl, halogen, O—$C_{1-6}$ alkyl, and $NR^pR^q$.

22. A compound according to formula I, or a salt or solvate thereof, according to any one of the preceding paragraphs wherein $R^5$ is selected from the group consisting of hydrogen, hydroxyl, halogen, O—$C_{1-6}$ alkyl, $NH_2$, NHMe, and $NMe_2$.

23. A compound according to formula I, or a salt or solvate thereof, according to any one of the preceding paragraphs wherein $R^5$ is selected from hydrogen, halogen and O—$C_{1-6}$ alkyl.

24. A compound according to formula I, or a salt or solvate thereof, according to any one of the preceding paragraphs wherein $R^5$ is selected from hydrogen, halogen and O—$C_{1-3}$ alkyl.

25. A compound according to formula I, or a salt or solvate thereof, according to any one of the preceding paragraphs wherein $R^5$ is selected from hydrogen, halogen and OMe.

26. A compound according to formula I, or a salt or solvate thereof, according to any one of the preceding paragraphs wherein $R^5$ is selected from hydrogen and halogen.

27. A compound according to formula I, or a salt or solvate thereof, according to any one of the preceding paragraphs wherein $R^6$ is selected from the group consisting of hydrogen, hydroxyl, halogen, $C_{1-6}$haloalkyl, $C_{1-6}$haloalkoxy, O—$C_{1-6}$ alkyl, $C_{1-6}$ alkyl and $NR^pR^q$.

28. A compound according to formula I, or a salt or solvate thereof, according to any one of the preceding paragraphs wherein $R^6$ is selected from the group consisting of hydrogen, hydroxyl, halogen, O—$C_{1-6}$ alkyl, $C_{1-6}$ alkyl and $NR^pR^q$.

29. A compound according to formula I, or a salt or solvate thereof, according to any one of the preceding paragraphs wherein $R^6$ is selected from the group consisting of hydrogen, hydroxyl, halogen, O—$C_{1-6}$ alkyl, $NH_2$, NHMe, and $NMe_2$.

30. A compound according to formula I, or a salt or solvate thereof, according to any one of the preceding paragraphs wherein $R^6$ is selected from the group consisting of hydrogen, halogen and O—$C_{1-6}$ alkyl.

31. A compound according to formula I, or a salt or solvate thereof, according to any one of the preceding paragraphs wherein $R^6$ is selected from hydrogen, halogen and O—$C_{1-3}$ alkyl.

32. A compound according to formula I, or a salt or solvate thereof, according to any one of the preceding paragraphs wherein $R^6$ is selected from hydrogen, halogen and OMe.

33. A compound according to formula I, or a salt or solvate thereof, according to any one of the preceding paragraphs wherein $R^6$ is selected from hydrogen and OMe.

34. A compound according to formula I or a salt or solvate thereof, according to any one of the preceding paragraphs wherein $R^{7a}$, $R^{7b}$ and $R^{7c}$ are independently selected from the group consisting of hydrogen, hydroxyl, halogen, CN, $C_{1-6}$ haloalkyl, $C_{1-6}$ haloalkoxy, O—$C_{1-6}$ alkyl and $C_{1-6}$ alkyl 35. A compound according to formula I, or a salt or solvate thereof, according to any one of the preceding paragraphs wherein $R^{7a}$, $R^{7b}$ and $R^{7c}$ are independently selected from the group consisting of hydrogen, hydroxyl, halogen, O—$C_{1-6}$ alkyl and $C_{1-6}$ alkyl.

36. A compound according to formula I, or a salt or solvate thereof, according to any one of the preceding paragraphs wherein $R^{7a}$, $R^{7b}$ and $R^{7c}$ are independently selected from the group consisting of hydrogen, hydroxyl, halogen, O—$C_{1-3}$ alkyl and $C_{1-3}$ alkyl.

37. A compound according to formula I, or a salt or solvate thereof, according to any one of the preceding paragraphs wherein $R^{7a}$, $R^{7b}$ and $R^{7c}$ are independently selected from hydrogen, halogen, O—$C_{1-3}$ alkyl and $C_{1-3}$ alkyl.

38. A compound according to formula I, or a salt or solvate thereof, according to any one of the preceding paragraphs wherein $R^{7a}$, $R^{7b}$ and $R^{7c}$ are independently selected from hydrogen, halogen and OMe.

39. A compound according to formula I, or a salt or solvate thereof, according to any one of the preceding paragraphs wherein $R^{7a}$, $R^{7b}$ and $R^{7c}$ are all hydrogen.

40. A compound according to formula I, or a salt or solvate thereof, according to any one of the preceding paragraphs wherein $R^4$ is selected from hydrogen or methyl.

41. A compound according to formula I, or a salt or solvate thereof, according to any one of the preceding paragraphs wherein $R^4$ is hydrogen.

42. A compound according to formula I, or a salt or solvate thereof, according to any one of the preceding paragraphs wherein $R^8$ is selected from the group consisting of hydrogen, hydroxyl, halogen, CN, $C_{1-6}$haloalkyl, $C_{1-6}$haloalkoxy, $C_{1-6}$ alkyl, and O—$C_{1-6}$ alkyl.

43. A compound according to formula I, or a salt or solvate thereof, according to any one of the preceding paragraphs wherein $R^8$ is selected from the group consisting of hydrogen, hydroxyl, halogen, $C_{1-6}$ alkyl, and O—$C_{1-6}$ alkyl.

44. A compound according to formula I, or a salt or solvate thereof, according to any one of the preceding paragraphs wherein $R^8$ is selected from hydrogen, halogen and $C_{1-6}$ alkyl.

45. A compound according to formula I, or a salt or solvate thereof, according to any one of the preceding paragraphs wherein $R^8$ is selected from hydrogen, halogen and methyl.

46. A compound according to formula I, or a salt or solvate thereof, according to any one of the preceding paragraphs wherein $R^8$ is hydrogen.

47. A compound according to formula I, or a salt or solvate thereof, according to any one of the preceding paragraphs wherein $R^9$ is selected from the group consisting of hydroxyl, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)N$R^cR^d$, —N$R^cR^d$, —N$R^c$C(=O)$R^d$, —N$R^c$S(=O)$_2R^d$, —O$R^d$, —S$R^d$, —OC(=O)$R^d$, —S(=O)$_2R^d$, —S(=O)$R^d$, —S(=O)N$R^cR^d$, and S(=O)$_2$N$R^cR^d$; wherein said $C_{3-6}$cycloalkyl, $C_{1-6}$alkyl, and 3-10 membered heterocycloalkyl are optionally substituted with one or more groups selected from hydroxyl, halogen, =O, CN, HNMe, NMe$_2$, $C_{1-6}$haloalkyl, $C_{1-6}$haloalkoxy, $C_{3-6}$cycloalkyl, $C_{1-6}$alkyl, and O—$C_{1-6}$alkyl; or a group of Formula II.

48. A compound according to formula I, or a salt or solvate thereof, according to any one of the preceding paragraphs wherein $R^9$ is selected from the group consisting of hydroxyl, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, —C(=O)$R^d$, —C(=O)O$R^d$, —C(=O)N$R^cR^d$, —N$R^cR^d$, —N$R^c$C(=O)$R^d$, —O$R^d$, —OC(=O)$R^d$; wherein said $C_{3-6}$cycloalkyl, $C_{1-6}$ alkyl, and 3-10 membered heterocycloalkyl are optionally substituted with one or more groups selected from hydroxyl, halogen, =O, CN, HNMe, NMe$_2$, $C_{1-6}$ haloalkyl, $C_{1-6}$ haloalkoxy, $C_{3-6}$ cycloalkyl, $C_{1-6}$ alkyl, and O—$C_{1-6}$ alkyl; or a group of Formula II.

49. A compound according to formula I, or a salt or solvate thereof, according to any one of the preceding paragraphs wherein $R^9$ is selected from the group consisting of hydroxyl, halogen, CN, $C_{1-6}$ haloalkyl, $C_{1-6}$ haloalkoxy, $C_{1-6}$ alkyl, O—$C_{1-6}$ alkyl, —C(=O)$R^d$, —C(=O)O$R^d$, —C(=O)N$R^cR^d$, —N$R^cR^d$, —N$R^c$C(=O)$R^d$, —O$R^d$, —OC(=O)$R^d$; wherein said $C_{1-6}$ alkyl is optionally substituted with one or more groups selected from hydroxyl, halogen, =O, CN, HNMe, NMe$_2$, $C_{1-6}$ haloalkyl, $C_{1-6}$ haloalkoxy, $C_{3-6}$ cycloalkyl, $C_{1-6}$ alkyl, and O—$C_{1-6}$ alkyl; or a group of Formula II.

50. A compound according to formula I, or a salt or solvate thereof, according to any one of the preceding paragraphs wherein $R^9$ is selected from the group consisting of hydroxyl, halogen, $C_{1-6}$ alkyl, O—$C_{1-6}$ alkyl, —C(=O)$R^d$, —C(=O)O$R^d$, —C(=O)N$R^cR^d$, —N$R^cR^d$, —N$R^c$C(=O)$R^d$, —O$R^d$, —OC(=O)$R^d$; wherein said $C_{1-6}$ alkyl is optionally substituted with one or more groups selected from hydroxyl, halogen, =O, CN, HNMe, NMe$_2$, $C_{1-6}$ haloalkyl, $C_{1-6}$ haloalkoxy, $C_{3-6}$cycloalkyl, $C_{1-6}$alkyl, and O—$C_{1-6}$alkyl; or a group of Formula II.

51. A compound according to formula I, or a salt or solvate thereof, according to any one of the preceding paragraphs wherein $R^9$ is selected from the group consisting of hydroxyl, halogen, $C_{1-6}$alkyl, O—$C_{1-6}$alkyl, —N$R^cR^d$, —O$R^d$, wherein said $C_{1-6}$alkyl is optionally substituted with one or more groups selected from hydroxyl, halogen, =O, CN, HNMe, NMe$_2$, $C_{1-6}$haloalkyl, $C_{1-6}$haloalkoxy, $C_{3-6}$ cycloalkyl, $C_{1-6}$ alkyl, and O—$C_{1-6}$ alkyl; or a group of Formula II.

52. A compound according to formula I, or a salt or solvate thereof, according to any one of the preceding paragraphs wherein $R^9$ is selected from the group consisting of $C_{1-6}$ alkyl, optionally substituted with one or more groups selected from hydroxyl, halogen, CN, HNMe, NMe$_2$, $C_{1-6}$ haloalkyl, $C_{1-6}$ haloalkoxy, $C_{3-6}$ cycloalkyl, $C_{1-6}$ alkyl, and O—$C_{1-6}$ alkyl; or a group of Formula II, and $R^8$ is selected from hydrogen and $C_{1-6}$ alkyl.

53. A compound according to formula I, or a salt or solvate thereof, according to any one of the preceding paragraphs, or a salt or solvate thereof, wherein $_a$, $_b$, $_c$ and $_d$ are independently selected from 0, 1, 2, suitably 0 and 1.

54. A compound according to formula I, or a salt or solvate thereof, according to any one of the preceding paragraphs wherein $_a$ is 0 and $_b$ is selected from 0, 1 and 2, suitably 0 and 1, more suitably 0.

55. A compound according to formula I, or a salt or solvate thereof, according to any one of the preceding paragraphs wherein $_a$ is selected from 0, 1 and 2, suitably 0 and 1, and $_b$ is 0.

56. A compound according to formula I, or a salt or solvate thereof, according to any one of the preceding paragraphs wherein $J^{1a}$ is selected from a direct bond, CH$_2$, O, NR$^{s1}$C(O), C(O)NR$^{s1}$, NR$^{s1}$C(O)NR$^{s1}$ and NR$^{s1}$.

57. A compound according to formula I, or a salt or solvate thereof, according to any one of the preceding paragraphs wherein $J^{1a}$ is selected from a direct bond, O, CH$_2$, NR$^{s1}$C(O), C(O)NR$^{s1}$ and NR$^{s1}$.

58. A compound according to formula I, or a salt or solvate thereof, according to any one of the preceding paragraphs wherein $J^{1a}$ is selected from a CH$_2$, NR$^{s1}$C(O), C(O)NR$^{s1}$ and NR$^{s1}$.

59. A compound according to formula I, or a salt or solvate thereof, according to any one of the preceding paragraphs wherein $J^{1a}$ is selected from a NR$^{s1}$C(O) and C(O)NR$^{s1}$.

60. A compound according to formula I, or a salt or solvate thereof, according to any one of the preceding paragraphs wherein $A^{1a}$ is selected from the group consisting of phenyl optionally substituted by one or more $R^k$, 5-6 membered heterocycloalkyl optionally substituted by one or more R and 5-6 membered heteroaryl optionally substituted by one or more $R^k$.

61. A compound according to formula I, or a salt or solvate thereof, according to any one of the preceding paragraphs wherein $A^{1a}$ is selected from the group consisting of phenyl optionally substituted by one or more $R^k$, pyridyl optionally substituted by one or more $R^K$, and morpholine, piperidine or piperazine each optionally substituted by one or more $R^k$.

62. A compound according to formula I, or a salt or solvate thereof, according to any one of the preceding paragraphs wherein $A^{1a}$ is selected from the group consisting of phenyl optionally substituted by one or more $R^k$, and 5-6 membered heterocycloalkyl optionally substituted by one or more $R^k$.

63. A compound according to formula I, or a salt or solvate thereof, according to any one of the preceding paragraphs wherein $A^{1a}$ is selected the group consisting of phenyl optionally substituted by one or more $R^k$, and morpholine, piperidine or piperazine each optionally substituted by one or more $R^k$.

64. A compound according to formula I, or a salt or solvate thereof, according to any one of the preceding paragraphs wherein $R^k$ is selected from the group consisting of hydrogen, $C_{1-6}$ alkyl, benzyl, CH$_2$heteroaryl, 3-10 membered heterocycloalkyl, —C(=O)R$^d$, —C(=O)NR$^c$R$^d$, and —NR$^c$R$^d$, where said C$_{1-6}$alkyl, benzyl, CH$_2$heteroaryl and 3-10 membered heterocycloalkyl are optionally substituted with one or more groups selected from hydroxyl, halogen, =O, CN, C$_{1-6}$ haloalkyl, C$_{1-6}$ haloalkoxy, C$_{3-6}$ cycloalkyl, NR$^c$R$^d$, 5-6 membered heterocycloalkyl, C$_{1-6}$ alkyl, and O—C$_{1-6}$ alkyl.

65. A compound according to formula I, or a salt or solvate thereof, according to any one of the preceding paragraphs wherein R$^k$ is selected from the group consisting of hydrogen, C$_{1-6}$ alkyl, 3-10 membered heterocycloalkyl, benzyl, —C(=O)R$^d$, —C(=O)NR$^c$R$^d$, and —NR$^c$R$^d$, where said C$_{1-6}$ alkyl and 3-10 membered heterocycloalkyl are optionally substituted with one or more groups selected from hydroxyl, halogen, =O, CN, haloalkyl, C$_{1-6}$ haloalkoxy, C$_{3-6}$ cycloalkyl, NR$^c$R$^d$, 5-6 membered heterocycloalkyl, C$_{1-6}$alkyl, and O—C$_{1-6}$alkyl.

66. A compound according to formula I, or a salt or solvate thereof, according to any one of the preceding paragraphs wherein R$^k$ is selected from the group consisting of hydrogen, C$_{1-6}$ alkyl, benzyl, —C(=O)R$^d$, —C(=O)NR$^c$R$^d$, and —NR$^c$R$^d$, where said C$_{1-6}$ alkyl is optionally substituted with one or more groups selected from hydroxyl, halogen, =O, CN, C$_{1-6}$ haloalkyl, C$_{1-6}$haloalkoxy, C$_{3-6}$cycloalkyl, NR$^c$R$^d$, and O—C$_{1-6}$alkyl.

67. A compound according to formula I, or a salt or solvate thereof, according to any one of the preceding paragraphs wherein R$^k$ is selected from the group consisting of hydrogen, benzyl, C$_{1-6}$ alkyl, —C(=O)R$^d$, —C(=O)NR$^c$R$^d$, and —NR$^c$R$^d$, where said C$_{1-6}$ alkyl is optionally substituted with one or more groups selected from C$_{1-6}$ haloalkyl, C$_{1-6}$ haloalkoxy, C$_{3-6}$ cycloalkyl, NR$^c$R$^d$, and O—C$_{1-6}$ alkyl.

68. A compound according to formula I, or a salt or solvate thereof, according to any one of the preceding paragraphs wherein $_y$ is 0.

69. A compound according to formula I, or a salt or solvate thereof, according to any one of the preceding paragraphs wherein $_y$ is 1.

70. A compound according to formula I, or a salt or solvate thereof, according to any one of the preceding paragraphs wherein R$^k$ is hydrogen and $_y$ is 1.

71. A compound according to formula I, or a salt or solvate thereof, according to any one of the preceding paragraphs wherein $_y$ is 0, and R$^k$ is selected from the group consisting of C$_{1-6}$alkyl, 3-10 membered heterocycloalkyl, —C(=O)R$^d$, —C(=O)NR$^c$R$^d$, and —NR$^c$R$^d$, where said C$_{1-6}$ alkyl and 3-10 membered heterocycloalkyl are optionally substituted with one or more groups selected from hydroxyl, halogen, =O, CN, C$_{1-6}$ haloalkyl, C$_{1-6}$ haloalkoxy, C$_{3-6}$ cycloalkyl, NR$^c$R$^d$, C$_{1-6}$alkyl, and O—C$_{1-6}$alkyl.

72. A compound according to formula I, or a salt or solvate thereof, according to any one of the preceding paragraphs wherein $_y$ is 0, and R$^k$ is selected from the group consisting of C$_{1-6}$alkyl, —C(=O)R$^d$, —C(=O)NR$^c$R$^d$, and —NR$^c$R$^d$, where said C$_{1-6}$alkyl is optionally substituted with one or more groups selected from hydroxyl, halogen, =O, CN, C$_{1-6}$ haloalkyl, haloalkoxy, C$_{3-6}$ cycloalkyl, NR$^c$R$^d$, 5-6 membered heterocycloalkyl, and O—C$_{1-6}$ alkyl.

73. A compound according to formula I, or a salt or solvate thereof, according to any one of the preceding paragraphs wherein $_c$ is selected from 0 and 1 and $_d$ is selected from 0 and 1.

74. A compound according to formula I, or a salt or solvate thereof, according to any one of the preceding paragraphs wherein $_c$ and $_d$ is 0, or $_c$ and $_d$ is 1.

75. A compound according to formula I, or a salt or solvate thereof, according to any one of the preceding paragraphs wherein $_c$ is 0 and $_d$ is 1, or $_c$ is 1 and $_d$ is 0.

76. A compound according to formula I, or a salt or solvate thereof, according to any one of the preceding paragraphs wherein R$^e$, R$^f$, R$^g$, R$^h$, R$^i$, R$^j$, R$^l$, R$^m$ are independently selected from methyl, ethyl and hydrogen.

77. A compound according to formula I, or a salt or solvate thereof, according to any one of the preceding paragraphs wherein R$^e$, R$^f$, R$^g$, R$^h$, R$^i$, R$^j$, R$^l$, R$^m$ are hydrogen.

78. A compound according to formula I, or a salt or solvate thereof, according to any one of the preceding paragraphs wherein J$^{1b}$ is selected from a direct bond, NR$^{s1}$C(O), NR$^{s1}$C(O)O and NR$^{s1}$.

79. A compound according to formula I, or a salt or solvate thereof, according to any one of the preceding paragraphs wherein J$^{1b}$ is selected from NR$^{s1}$C(O), NR$^{s1}$C(O)O and NR$^{s1}$.

80. A compound according to formula I, or a salt or solvate thereof, according to any one of the preceding paragraphs wherein R$^{s1}$ is independently selected from hydrogen, methyl and ethyl.

81. A compound according to any one of the preceding paragraphs, or a salt or solvate thereof, wherein R$^{s1}$ is hydrogen.

82. A compound according to formula I, or a salt or solvate thereof, according to any one of the preceding paragraphs wherein A$^{1b}$ is selected from the group consisting of C$_{6-11}$ aryl optionally substituted by one or more R$^r$, 3-15 membered heterocycloalkyl optionally substituted by one or more R$^r$, and 5-15 membered heteroaryl optionally substituted by one or more R$^r$.

83. A compound according to formula I, or a salt or solvate thereof, according to any one of the preceding paragraphs wherein A$^{1b}$ is selected from the group consisting of phenyl optionally substituted by one or more R$^r$, 5-6 membered heterocycloalkyl optionally substituted by one or more R$^r$, and a 5-6 membered heteroaryl optionally substituted by one or more R$^r$.

84. A compound according to formula I, or a salt or solvate thereof, according to any one of the preceding paragraphs wherein A$^{1b}$ is selected from the group consisting of phenyl optionally substituted by one or more R$^r$, pyridyl optionally substituted by one or more R$^r$, and morpholine, piperidine or piperazine each optionally substituted by one or more R$^r$.

85. A compound according to formula I, or a salt or solvate thereof, according to any one of the preceding paragraphs wherein R$^r$ is selected from the group consisting of hydrogen, C$_{1-6}$ alkyl, benzyl, CH$_2$heteroaryl, 3-10 membered heterocycloalkyl, —C(=O)R$^d$, —C(=O)NR$^c$R$^d$, and —NR$^c$R$^d$, where said C$_{1-6}$alkyl, benzyl, CH$_2$heteroaryl and 3-10 membered heterocycloalkyl are optionally substituted with one or more groups selected from hydroxyl, halogen, =O, CN, C$_{1-6}$ haloalkyl, C$_{1-6}$ haloalkoxy, C$_{3-6}$ cycloalkyl, NR$^c$R$^d$, 5-6 membered heterocycloalkyl, C$_{1-6}$ alkyl, and O—C$_{1-6}$ alkyl.

86. A compound according to formula I, or a salt or solvate thereof, according to any one of the preceding paragraphs wherein $R^r$ is selected from the group consisting of hydrogen, $C_{1-6}$alkyl, 3-10 membered heterocycloalkyl, —C(=O)$R^d$, —C(=O)N$R^cR^d$, and —N$R^cR^d$, where said $C_{1-6}$ alkyl and 3-10 membered heterocycloalkyl are optionally substituted with one or more groups selected from hydroxyl, halogen, =O, CN, haloalkyl, $C_{1-6}$ haloalkoxy, $C_{3-6}$ cycloalkyl, N$R^cR^d$, 5-6 membered heterocycloalkyl, $C_{1-6}$alkyl, and O—$C_{1-6}$alkyl.

87. A compound according to formula I, or a salt or solvate thereof, according to any one of the preceding paragraphs wherein $R^r$ is selected from the group consisting of hydrogen, $C_{1-6}$ alkyl, —C(=O)$R^d$, —C(=O)N$R^cR^d$, and —N$R^cR^d$, where said $C_{1-6}$ alkyl is optionally substituted with one or more groups selected from hydroxyl, halogen, =O, CN, $C_{1-6}$ haloalkyl, $C_{1-6}$ haloalkoxy, $C_{3-6}$cycloalkyl, N$R^cR^d$, and O—$C_{1-6}$alkyl.

88. A compound according to formula I, or a salt or solvate thereof, according to any one of the preceding paragraphs wherein $R^r$ is selected from the group consisting of hydrogen, $C_{1-6}$ alkyl, —C(=O)$R^d$, —C(=O)N$R^cR^d$, and —N$R^cR^d$, where said $C_{1-6}$ alkyl is optionally substituted with one or more groups selected from $C_{1-6}$ haloalkyl, $C_{1-6}$ haloalkoxy, $C_{3-6}$ cycloalkyl, N$R^cR^d$, and O—$C_{1-6}$ alkyl.

89. A compound according to formula I, or a salt or solvate thereof, according to any one of the preceding paragraphs wherein $R^c$ is independently selected from hydrogen and $C_{1-6}$ alkyl.

90. A compound according to formula I, or a salt or solvate thereof, according to any one of the preceding paragraphs wherein $R^d$ is independently selected from the group consisting of hydrogen, 3-10 membered heterocycloalkyl, and $C_{1-6}$ alkyl, wherein said $C_{1-6}$ alkyl and 3-10 membered heterocycloalkyl are optionally substituted with one or more groups selected from hydroxyl, =O, halogen, CN, $NH_2$, NHMe, $NMe_2$, $C_{1-6}$ haloalkyl, $C_{3-6}$ cycloalkyl, $C_{6-11}$ aryl, $C_{1-6}$ alkyl and O—$C_{1-6}$alkyl.

91. A compound according to formula I, or a salt or solvate thereof, according to any one of the preceding paragraphs wherein $R^d$ is independently selected from the group consisting of hydrogen, 3-7 membered heterocycloalkyl, and $C_{1-6}$ alkyl, wherein said $C_{1-6}$ alkyl and 3-7 membered heterocycloalkyl are optionally substituted with one or more groups selected from hydroxyl, =O, halogen, CN, $NH_2$, NHMe, $NMe_2$, $C_{1-6}$ haloalkyl, $C_{3-6}$ cycloalkyl, $C_{6-11}$ aryl, $C_{1-6}$ alkyl and O—$C_{1-6}$alkyl.

92. A compound according to formula I, or a salt or solvate thereof, according to any one of the preceding paragraphs wherein $R^d$ is independently selected from the group consisting of hydrogen, 5-6 membered heterocycloalkyl, and $C_{1-6}$ alkyl, wherein said $C_{1-6}$ alkyl and 5-6 membered heterocycloalkyl are optionally substituted with one or more groups selected from hydroxyl, =O, halogen, CN, $NH_2$, NHMe, $NMe_2$, $C_{1-6}$ haloalkyl, $C_{3-6}$cycloalkyl, phenyl, $C_{1-6}$alkyl and O—$C_{1-6}$ alkyl.

93. A compound according to formula I, or a salt or solvate thereof, according to any one of the preceding paragraphs wherein $R^c$ and $R^d$, when attached to the same atom, together with the atom to which they are attached form a 5-6 membered ring, optionally containing one or more for heteroatoms selected from O, NH and S, and wherein said ring is optionally substituted with one or more $R^a$.

94. A compound, or a salt or solvate thereof, selected from:
N-(4-((dimethylamino)methyl)phenyl)-3'-methoxy-[1,1'-biphenyl]-4-amine;
N-(4-((dimethylamino)methyl)phenyl)-3,3'-dimethoxy-[1,1'-biphenyl]-4-amine;
N-(4-((dimethylamino)methyl)phenyl)-2-fluoro-3,3'-dimethoxy-[1,1'-biphenyl]-4-amine;
N-(4-((dimethylamino)methyl)phenyl)-4'-fluoro-3'-methoxy-[1,1'-biphenyl]-4-amine;
N-(4-((dimethylamino)methyl)phenyl)-3',4'-difluoro-5'-methoxy-[1,1'-biphenyl]-4-amine;
N-(4-((dimethylamino)methyl)phenyl)-3'-fluoro-5'-methoxy-[1,1'-biphenyl]-4-amine;
N-(4-((dimethylamino)methyl)phenyl)-3'-methoxy-5'-methyl-[1,1'-biphenyl]-4-amine;
N-(3,5-dimethylphenyl)-2-fluoro-3,3'-dimethoxy-[1,1'-biphenyl]-4-amine;
N-(3,5-dimethylphenyl)-3'-methoxy-[1,1'-biphenyl]-4-amine;
3-((3'-methoxy-[1,1'-biphenyl]-4-yl)amino)-N,N,4-trimethylbenzamide;
N-(5-((dimethylamino)methyl)-2-methylphenyl)-3'-methoxy-[1,1'-biphenyl]-4-amine;
N-(3-((2,6-dimethylmorpholino)methyl)phenyl)-3'-methoxy-[1,1'-biphenyl]-4-amine;
N-(4-((2,6-dimethylmorpholino)methyl)phenyl)-3'-methoxy-[1,1'-biphenyl]-4-amine;
N-(4-((dimethylamino)methyl)phenyl)-2-methoxy-6-(3-methoxyphenyl)pyridin-3-amine
N-(3-((dimethylamino)methyl)phenyl)-2-methoxy-6-(3-methoxyphenyl)pyridin-3-amine
N-(4-((dimethylamino)methyl)phenyl)-6-(3-methoxyphenyl)pyridin-3-amine;
3-((3'-methoxy-[1,1'-biphenyl]-4-yl)amino)-N-(piperidin-4-ylmethyl)benzamide;
N-(4-((dimethylamino)methyl)phenyl)-3'-methoxy-4'-methyl-[1,1'-biphenyl]-4-amine;
N-((1-benzylpiperidin-4-yl)methyl)-4-((3'-methoxy-[1,1'-biphenyl]-4-yl)amino)benzamide;
4-((3'-methoxy-[1,1'-biphenyl]-4-yl)amino)-N-(piperidin-4-ylmethyl)benzamide;
N-((1-benzylpiperidin-4-yl)methyl)-4-((3'-methoxy-[1,1'-biphenyl]-4-yl)amino)benzamide;
4-((3'-methoxy-[1,1'-biphenyl]-4-yl)amino)-N-((1-methylpiperidin-4-yl)methyl)benzamide; and
4-((3',4'-difluoro-5'-methoxy-[1,1'-biphenyl]-4-yl)amino)-N-((1-methylpiperidin-4-yl)methyl)benzamide.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I may exist in solvated as well as unsolvated forms such as, for example, hydrated forms. It is to be understood that the invention encompasses all such solvated forms that possess antiproliferative activity.

Polymorphs

It is also to be understood that certain compounds of the Formula I may exhibit polymorphism, and that the invention encompasses all such forms that possess antiproliferative activity.

N-Oxides

Compounds of the Formula I containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the Formula I may exist in a number of different tautomeric forms and references to compounds of the Formula I include all such forms. For the avoidance of doubt, where a compound can exist in one of several tautomeric forms, and only one is specifically described or shown, all others are nevertheless embraced by Formula I. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/acinitro.

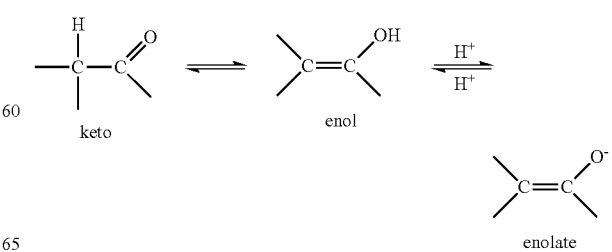

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);

b) Design of Pro-drugs, edited by H. Bundgaard, (Elsevier, 1985);

c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews*, 8, 1-38 (1992);

e) H. Bundgaard, et al, *Journal of Pharmaceutical Sciences*, 77, 285 (1988);

f) N. Kakeya, et al, *Chem. Pharm. Bull.*, 32, 692 (1984);

g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-6}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I that possesses a carboxy group is, for example, an in vivo cleavable amide thereof, for example an amide formed with an amine such as ammonia, a $C_{1-4}$alkylamine such as methylamine, a $(C_{1-4}alkyl)_2$amine such as dimethylamine, N-ethyl-N-methylamine or diethylamine, a $C_{1-4}$ alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the Formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-yl methyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt or solvate thereof, and one or more pharmaceutically acceptable excipients.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of RAS-effector protein-protein interaction.

The present invention therefore provides a method of inhibiting a RAS-effector protein-protein interaction in vitro or in vivo, said method comprising contacting a cell with an effective amount of a compound, or a pharmaceutically acceptable salt, hydrate or solvate thereof, as defined herein.

The present invention also provides a method of treating a disease or disorder in aberrant RAS-effector interaction is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of a RAS-effector protein-protein interaction, suitably an aberrant RAS-effector protein-protein interaction.

The present invention provides a compound, or a pharmaceutically acceptable salt, hydrate or solvate thereof, as defined herein for use in the treatment of a disease or disorder in which aberrant RAS-effector protein-protein interaction is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of a RAS-effector protein-protein interaction, suitably an aberrant RAS-effector protein-protein interaction.

The present invention provides a use of a compound, or a pharmaceutically acceptable salt, hydrate or solvate thereof, as defined herein in the manufacture of a medicament for the treatment of a disease or disorder in which an aberrant RAS-effector protein-protein interaction is implicated.

The term "proliferative disorder" used herein pertains to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (for instance, by virtue of their inhibition of RAS-effector protein-protein interactions).

In one embodiment, the compounds inhibit interaction of RAS (suitably NRAS, KRAS or HRAS, more suitably KRAS) with one or more effector proteins.

In another embodiment, the compounds inhibit interaction of RAS with one or more effector proteins selected from PLCε (epsilon), PKCζ (zeta), PI3K, RASSF, RAF, RalGEF, RIN, AF-6, GAP and TIAM1, suitably selected from PI3K, RAF and RalGEF.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer. For example, lung cancer, colon cancer, rectum cancer, breast cancer, ovarian cancer, prostate cancer, liver cancer, pancreatic cancer, brain cancer and skin cancer.

In one embodiment, the cancer is selected from pancreatic cancer, colon cancer, rectum cancer and lung cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:— other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, $C_{225}$] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (Cl 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib ($R^{115777}$) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

vascular damaging agents such as Combretastatin A4 and compounds disclosed in International Patent Applications WO 99/02166, WO 00/40529, WO 00/41669, WO 01/92224, WO 02/04434 and WO 02/08213;

an endothelin receptor antagonist, for example zibotentan (ZD4054) or atrasentan;

antisense therapies, for example those which are directed to the targets listed above, such as ISIS 2503, an anti-ras antisense;

gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. In one embodiment, a combination refers to a combination product.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Chemistry

The following examples are provided solely to illustrate the present invention and are not intended to limit the scope of the invention, as described herein.

The compounds of the invention may be prepared using synthetic techniques that are known in the art (as illustrated by the examples herein).

Several methods for the chemical synthesis of the compounds of the present application are described herein. These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

Synthesis and Characterisation

Methods

All solvents and reagents were used as supplied (analytical or HPLC grade) without prior purification. Water was purified by an Elix® UV-10 system. Brine refers to a saturated aqueous solution of sodium chloride. In vacuo refers to the use of a rotary evaporator attached to a diaphragm pump.

Thin layer chromatography was performed on aluminium plates coated with 60 F254 silica. Plates were visualised using UV light (254 nm) or 1% aq. KMnO4. Flash column chromatography was performed on Kieselgel 60M silica in a glass column.

NMR spectra were recorded on Bruker Avance spectrometers (AVII400, AVIII 400, AVIII HD 600 or AVIII 700) in the deuterated solvent stated. The field was locked by external referencing to the relevant deuteron resonance. Chemical shifts (5) are reported in parts per million (ppm) referenced to the solvent peak. 1H spectra reported to two decimal places, and 13C spectra reported to one decimal place, and coupling constants (J) are quoted in Hz (reported to one decimal place). The multiplicity of each signal is indicated by: s (singlet); br. s (broad singlet); d (doublet); t (triplet); q (quartet); dd (doublet of doublets); td (triplet of doublets); qt (quartet of triplets); or m (multiplet).

Low-resolution mass spectra were recorded on an Agilent 6120 spectrometer from solutions of MeOH. Accurate mass measurements were run on either a Bruker MicroTOF internally calibrated with polyalanine, or a Micromass GCT instrument fitted with a Scientific Glass Instruments BPX5 column (15 m×0.25 mm) using amyl acetate as a lock mass, by the mass spectrometry department of the Chemistry Research Laboratory, University of Oxford, UK.; m/z values are reported in Daltons.

Abbreviations

The following abbreviations are used in the Examples and other parts of the description.

$Pd(dppf)Cl_2$: [1,1'-Bis(diphenylphosphino)ferrocene]dichloropalladium(II)

$K_2CO_3$: potassium carbonate $Cs_2CO_3$: cesium carbonate $Na_2SO_4$: sodium sulphate $Pd(OAc)_2$: pallsiaum acetate EtOAc: ethyl acetate h: hour(s)

min: minute(s)

NMR: Nuclear Magnetic Resonance

LRMS: Low resolution mass spectrometry

HRMS: High resolution mass spectrometry

XPhos: 2-dicyclohexylphosphino-2',4',6'-triisopropylbiphenyl

General Procedures

General Procedure A

The requisite halogen (600 mg, 2.79 mmol, 1.0 eq.), $K_2CO_3$ (1.16 g, 8.37 mmol, 3.0 eq.), the requisite boronic acid (572 mg, 3.07 mmol, 1.1 eq.), and $Pd(dppf)Cl_2$ (100 mg, 0.140 mmol, 5 mol %) were added sequentially to a microwave vial equipped with a magnetic stirrer bar. The reaction vessel was fitted with a rubber septum and purged with N2 for 5 min, before addition of a degassed solution of 1,4-dioxane/water (5:1, 8 mL) via syringe. The vial was then sealed and the reaction heated to 100° C. for 18 h. The mixture was cooled down, diluted with EtOAc (30 mL), and washed with a 50/50 solution of water and brine (2×30 mL). The organic phase was dried (Na2SO4) and concentrated in vacuo. Purification by column chromatography on silica gel (solvents as stated) afforded the desired product.

General Procedure B

The requisite halogen (75 mg, 0.272 mmol, 1.0 eq.), Cs2CO3 (266 mg, 0.866 mmol, 3.0 eq.), the requisite amine (53 mg, 0.354 mmol, 1.3 eq.), XPhos (13 mg, 0.027 mmol, 10 mol %) and Pd(OAc)2 (3 mg, 0.014 mmol, 5 mol %) were added sequentially to a microwave vial equipped with a magnetic stirrer bar. The reaction vessel was fitted with a rubber septum and purged with N2 for 5 min, before addition of a degassed solution of 1,4-dioxane (3 mL) via syringe. The vial was then sealed and the reaction heated to 100° C. for 24 h. The mixture was cooled down, diluted with EtOAc (30 mL), and washed with a 50/50 solution of water and brine (2×30 mL). The organic phase was dried (Na2SO4) and concentrated in vacuo. Purification by column chromatography on silica gel (solvents as stated) afforded the desired product.

Preparations

Preparation 1: Synthesis of 4'-chloro-3-methoxy-1,1'-biphenyl

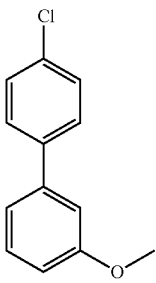

Following General Procedure A, 3-bromoanisole (200 mg, 1.07 mmol) and 4-chlorobenzylboronic acid (185 mg, 1.18 mmol) afforded the title product (231 mg, 99%) as a clear oil that solidified on standing after purification on silica gel (EtOAc:pentane (1:99)).

$^1$H NMR (600 MHz, CDCl$_3$) δ=7.52 (2H, dd, J 8.8, 0.7), 7.41 (2H, dd, J 8.8, 0.7), 7.36 (1H, dd, J 7.6, 0.7), 7.15 (1H, dquin, J 7.6, 0.7), 7.09 (1H, dt, J 2.6, 1.4), 6.92 (1H, ddt, J 8.3, 2.4, 1.0), 3.88 (3H, s); $^{13}$C NMR (125 MHz, CDCl$_3$) δ=160.0, 141.5, 139.5, 133.5, 129.9, 128.9, 128.4, 119.5, 112.9, 112.8, 55.3; LRMS (ESI+) 219.1 (M+H)$^+$.

Preparation 2: Synthesis of 4-chloro-3,3'-dimethoxy-1,1'-biphenyl

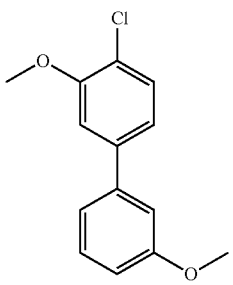

Following General Procedure A, 3-bromoanisole (200 mg, 1.07 mmol) and 4-chloro-3-methoxyphenyl boronic acid (220 mg, 1.18 mmol) afforded the title product (232 mg, 99%) as a beige solid after purification on silica gel (EtOAc:pentane (1:99)).

$^1$H NMR (600 MHz, CDCl$_3$) δ=7.42 (1H, dd, J 7.7, 0.7), 7.37 (1H, t, J 7.9), 7.16 (1H, dt, J 7.6, 0.9), 7.13 (1H, s), 7.11 (1H, ddd, J 11.4, 9.5, 2.0), 7.10 (1H, t, J 2.4), 6.93 (1H, dd, J 8.3, 2.6), 3.98 (3H, s), 3.88 (3H, s); $^{13}$C NMR (125 MHz, CDCl$_3$) δ=160.0, 155.1, 141.9, 141.2, 130.3, 129.9, 121.8, 120.1, 119.8, 113.1, 112.8, 111.1, 56.2, 55.4; LRMS (ESI+) 249.7 (M+H)$^+$.

Preparation 3: Synthesis of 4-chloro-2-fluoro-3,3'-dimethoxy-1,1'-biphenyl

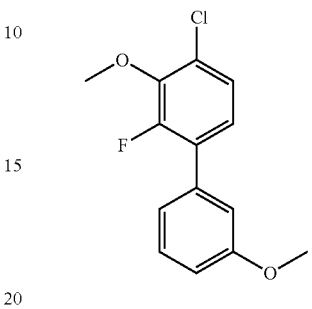

Following General Procedure A, 3-bromoanisole (200 mg, 1.07 mmol) and 4-chloro-2-fluoro-3-methoxyphenylboronic acid (241 mg, 1.18 mmol) afforded the title product (272 mg, 96%) as a yellow oil after purification on silica gel (EtOAc:pentane (1:99)).

$^1$H NMR (600 MHz, CDCl$_3$) δ=7.38 (1H, t, J 7.8), 7.22 (1H, dd, J 8.4, 1.8), 7.10 (1H, dd, J 8.6, 7.6), 710-7.09 (1H, m), 7.06 (1H, dd, J 2.7, 1.5), 6.95 (1H, ddd, J 8.3, 2.4, 1.0), 4.01 (3H, d, J 1.0), 3.86 (3H, s); $^{19}$F NMR (565 MHz, CDCl$_3$) δ=−132.4 (d, J 8.0); $^{13}$C NMR (125 MHz, CDCl$_3$) δ=159.6, 154.4, 152.7, 144.8 (d, J 14.3), 136.0, 129.5, 129.3 9d, J 13.2), 127.5 (d, J 2.2), 125.1 (d, J 3.3), 124.8 (d, J 3.3), 121.3 (d, J 2.2), 114.6 (d, J 2.2), 113.6, 61.6 (d, J 4.4), 55.3; LRMS (ESI+) 267.7 (M+H)$^+$.

Preparation 4: Synthesis of 4'-chloro-4-fluoro-3-methoxy-1,1'-biphenyl

Following General Procedure A, 5-bromo-2-fluoroanisole (200 mg, 0.956 mmol) and 4-chloropbenylboronic acid (164 mg, 1.05 mmol) afforded the title product (223 mg, 99%) as a yellow solid after purification on silica gel (EtOAc:pentane (1:49)).

$^1$H NMR (600 MHz, CDCl$_3$) δ=7.47 (2H, dt, J 8.4, 1.8), 7.41 (2H, dt, J 8.4, 2.6), 7.14 (1H, dd, J 11.0, 84), 7.12 (1H, dd, J 8.1, 2.2), 7.06 (1H, ddd, J 8.3, 4.4, 2.2), 3.96 (3H, s); $^{19}$F NMR (565 MHz, CDCl$_3$) δ=−136.9 (sxt, J 4.1); $^{13}$C NMR (125 MHz, CDCl$_3$) δ=153.1, 151.5, 147.8 (d, J 11.0), 139.0, 136.7 (d, J 4.4), 133.5, 118.5 (d, J 7.7), 116.4 (d, J 18.7), 112.4, 56.4; LRMS (ESI+) 237.7 (M+H)$^+$.

Preparation 5: Synthesis of 4'-chloro-3,4-difluoro-5-methoxy-1,1'-biphenyl

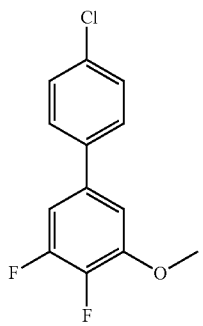 [SMILES: COc1cc(-c2ccc(Cl)cc2)cc(F)c1F]

Following General Procedure A, 5-bromo-2,3-difluoroanisole (200 mg, 0.896 mmol) and 4-chlorophenylboronic add (154 mg, 0.986 mmol) afforded the title product (212 mg, 93%) as a yellow solid after purification on silica gel (EtOAc:pentane (1:49)).
$^1$H NMR (600 MHz, CDCl$_3$) δ=7.45 (2H, dt, J 8.6, 2.2), 7.42 (2H, dt, J 8.6, 2.2), 6.95 (1H, ddd, J 10.7, 6.4, 2.2), 6.89 (1H, J 6.9, 1.9), 3.97 (3H, s); $^{19}$F NMR (565 MHz, CDCl$_3$) δ=−136.7 (q, J 10.2), −161.1 (dt, J 20.4, 8.2); $^{13}$C NMR (125 MHz, CDCl$_3$) δ=151.3 (dd, J 247.6, 11.0), 149.3 (dd, J 8.3, 3.9), 140.8 (dd, J 248.7, 14.3), 138.1, 135.9 (dd, J 8.3, 5.0), 134.1, 129.1, 128.2, 107.8 (d, J 18.7), 107.4 (d, J 2.2), 56.8; LRMS (ESI+) 255.7 (M+H)$^+$.

Preparation 6: Synthesis of 4'-chloro-3-fluoro-5-methoxy-1,1'-biphenyl

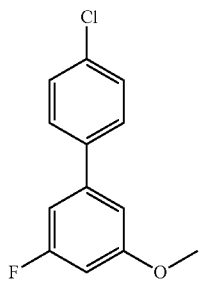 [SMILES: COc1cc(F)cc(-c2ccc(Cl)cc2)c1]

Following General Procedure A, 5-bromo-2-fluoroanisole (205 mg, 1.00 mmol) and 4-chlorophenylboronic acid (172 mg, 1.10 mmol) afforded the title product (227 mg, 96%) as a yellow solid after purification on silica gel (1:49)).
$^1$H NMR (600 MHz, CDCl$_3$) δ=7.49 (2H, ddd, J 8.4, 2.8, 1.8), 7.42 (2H, ddd, J 8.4, 2.8, 2), 6.88 (1H, t, J 1.8), 6.86 (1H, dt, J 8.4, 2.2), 6.63 (1H, dt, J 10.5, 2.3), 3.86 (3H, s); $^{19}$F NMR (565 MHz, CDCl$_3$) δ=−111.3 (t, J 10.2); $^{13}$C NMR (125 MHz, CDCl$_3$) δ=164.7, 163.1, 161.2 (d, J 12.1), 142.6 (d, J 9.9), 138.5 (d, J 3.3), 134.1, 129.0, 128.3, 108.8 (d, J 2.2), 106.3 (d, J 23.1), 100.5 (d, J 26.4), 55.6; LRMS (ESI+) 237.7 (M+H)$^+$.

Preparation 7: Synthesis of 4'-chloro-3-methoxy-5-methyl-1,1'-biphenyl

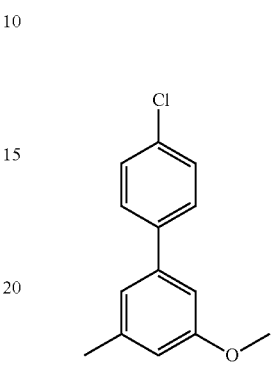

Following General Procedure A, 3-bromo-5-methylanisole (201 mg, 1.00 mmol) and 4-chlorophenylboronic acid (172 mg, 1.10 mmol) afforded the title product (228 mg, 97%) as a yellow solid after purification on silica gel (EtOAc:pentane (1:49)).
$^1$H NMR (600 MHz, CDCl$_3$) δ=7.51 (2H, d, J 8.6), 7.40 (2H, d, J 8.6), 6.97 (1H, s), 6.89 (1H, s), 6.74 (1H, s), 3.86 (3H, s), 2.40 (3H, s); $^{13}$C NMR (125 MHz, CDCl$_3$) δ=160.0, 141.3, 139.9, 139.7, 133.4, 128.8, 128.4, 120.4, 113.8, 109.9, 55.3, 21.6; LRMS (ESI+) 233.7 (M+H)$^+$.

Preparation 8: Synthesis of 3'-methoxy-[1,1'-biphenyl]-4-amine

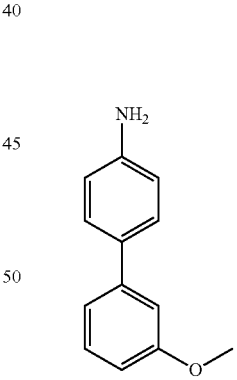

Following General Procedure A, 4-bromoaniline (400 mg, 2.32 mmol) and 3-methoxyphenylboronic acid (424 mg, 2.79 mmol) afforded the title product (228 mg, 97%) as a yellow solid after purification on silica gel (EtOAc:pentane (1:4)).
$^1$H NMR (600 MHz, MeOD) δ=7.37 (2H, dt, J 8.6, 2.6), 7.26 (1H, ddd, J 8.6, 7.7, 0.4), 7.09 (1H, ddd, J 7.7, 1.7, 1.0), 7.05 (1H, dd, J 2.6, 1.5), 6.81 (1H, dd, J 2.6, 1.0), 6.78 (2H, dt, J 8.7, 2.7), 3.82 (3H, s), NHs were not observed; $^{13}$C NMR (125 MHz, MeOD) δ=160.1, 147.1, 142.8, 130.7, 129.2, 127.2, 118.2, 115.3, 111.4, 111.0, 54.2. LRMS (ESI+) 200.3 (M+H)$^+$.

Preparation 9: Synthesis of 2-methoxy-6-(3-methoxyphenyl)pyridin-3-amine

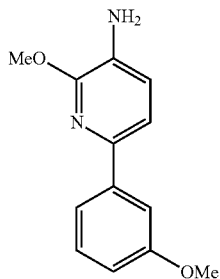 [SMILES: COc1cccc(-c2ccc(N)c(OC)n2)c1]

Following General Procedure A, 3-amino-6-bromo-2-methoxypyridine (200 mg, 0.983 mmol) and 3-methoxyphenylboronic acid (179 mg, 1.18 mmol) afforded the title product (208 mg, 92%) as a yellow solid after purification on silica gel (MeOH:CH$_2$Cl$_2$ (1:49)).

$^1$H NMR (600 MHz, MeOD) δ=7.54 (1H, dd, J 2.6, 1.7), 7.50 (1H, ddd, J 7.7, 1.6, 0.9), 7.27 (1H, t, J 7.9), 7.24 (1H, d, J 7.9), 7.00 (1H, d, J 7.9), 6.82 (1H, ddd, J 8.1, 2.6, 0.8), 4.06 (3H, s), 3.83 (3H, s), NHs were not observed; $^{13}$C NMR (125 MHz, MeOD) δ=161.6, 153.7, 143.6, 142.6, 132.5, 130.5, 122.0, 119.1, 114.8, 113.7, 112.3, 55.8, 53.6; LRMS (ESI+) 231.3 (M+H)$^+$.

Preparation 10: Synthesis of 6-(3-methoxyphenyl)pyridin-3-amine

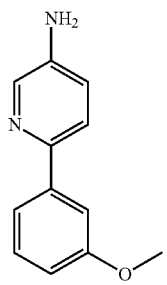

Following General Procedure A, 5-amino-2-chloropyridine (200 mg, 1.56 mmol) and 3-methoxyphenylboronic add (260 mg, 1.71 mmol) afforded the title product (282 mg, 90%) as a yellow oil after purification on silica gel (MeOH:CH$_2$Cl$_2$ (3:47)).

$^1$H NMR (400 MHz, MeOD) δ=8.03 (1H, dd, J 2.7 0.7), 7.51 (1H, dd, J 8.6, 0.7), 7.36 (1H, ddd, J 2.9, 1.5, 0.5), 7.33 (1H, dt, J 7.8, 1.5), 7.29 (1H, dd, J 7.6, 0.5), 7.12 (1H, dd, J 8.6, 2.9), 6.86 (1H, ddd, J 7.8, 2.6, 1.6), 3.81 (3H, s); NHs were not observed; $^{13}$C NMR (75 MHz, MeOD) δ=161.6, 147.7, 145.5, 142.3, 137.2, 130.8, 123.7, 123.0, 119.8, 114.5, 112.6, 55.8. LRMS (ESI$^-$) 199.1 (M–H)$^-$.

Preparation 11: Synthesis of 3'-methoxy-4'-methyl-[1,1'-biphenyl]-4-amine

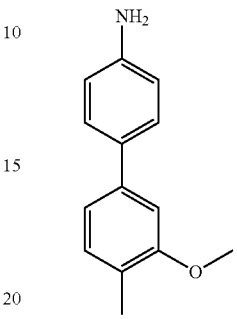

Following General Procedure A, 4-chlromethoxytoluene (200 mg, 1.28 mmol) and 4-aminophenylboronic add (244 mg, 1.40 mmol) afforded the title product (282 mg, 90%) as a pale yellow solid after purification on silica gel (EtOAc:pentane 1:4)).

$^1$H NMR (400 MHz, MeOD) δ=7.35 (2H, dt, J 8.6, 2.7), 7.08 (1H, dd, J 7.6, 1.0), 7.01 (1H, d, J 1.7), 6.98 (1H, dd, J 7.6, 1.7), 6.78 (2H, dt, J 8.6, 2.7), 3.85 (3H, s), 2.18 (3H, s), NHs were not observed; $^{13}$C NMR (75 MHz, MeOD) δ=159.5, 148.2, 141.9, 132.8, 131.8, 128.8, 125.4, 119.2, 116.9, 109.2, 55.9, 16.1; LRMS (ESI+) 314.3 (M+H)$^+$.

Preparation 12: Synthesis of 4'-chloro-3-methoxy-4-methyl-1,1'-biphenyl

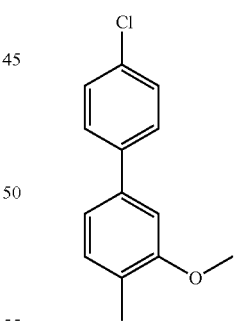

Following General Procedure A, 5-chloro-2-methylanisole (157 mg, 1.00 mmol) and 4-chlorobenzylboronic acid (172 mg, 1.10 mmol) afforded the title product (224 mg, 97%) as a clear oil that solidified on standing after purification on silica gel (EtOAc:pentane (1:99)).

$^1$H NMR (400 MHz, CDCl$_3$) δ=7.49 (2H, d, J 83), 7.42 (2H, d, J 8.3), 7.04 (1H, d, J 7.9), 6.85 (1H, dd, J 7.9, 2.0), 6.81 (1H, d, J 2.0), 3.83 (3H, s), 2.18 (3H, s); $^{13}$C NMR (75 MHz, CDCl$_3$) δ=158.2, 138.4, 133.7, 131.9, 131.1, 129.0, 128.2, 127.0, 125.1, 120.1, 110.7, 55.5; LRMS (ESI+) 233.7 (M+H)$^+$.

EXAMPLES

Example 1: Synthesis of N-(4-((dimethylamino)methyl)phenyl)-3'-methoxy-[1,1'-biphenyl]-4-amine

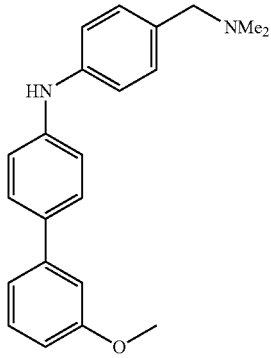 [SMILES: COc1cccc(-c2ccc(Nc3ccc(CN(C)C)cc3)cc2)c1]

Following General Procedure B, the product of preparation 1 (155 mg, 0.711 mmol) and 4-amino-N,N-dimethylbenzylamine (128 mg, 0.853 mmol) afforded the title product (209 mg, 88%) as a yellow oil that solidified on standing after purification on silica gel (MeOH:CH$_2$Cl$_2$ (1:9)).

$^1$H NMR (600 MHz, MeOD) δ=7.50 (2H, d, J 8.4), 7.30 (1H, t, J 8.0), 7.20 (2H, d, J 8.3), 7.16 (2H, d, J 8.4), 7.15 (2H, d, J 8.8), 7.11 (2H, d, J 8.3), 6.83 (1H, dd, J 8.3, 2.4), 3.84 (3H, s), 3.51 (2H, s), 2.32 (6H, s), NH was not observed; $^{13}$C NMR (125 MHz, MeOD) δ=161.7, 145.0, 144.7, 134.3, 132.1, 130.9, 129.1, 128.8, 119.8, 118.7, 118.3, 113.1, 113.0, 64.3, 55.8, 44.8; LRMS (ESI+) 333.1 (M+H)$^+$; HRMS (ESI$^+$) [C$_{22}$H$_{25}$N$_2$O] requires 333.4550, found 333.4538;

Example 2: Synthesis of N-(4-((dimethylamino)methyl)phenyl)-3,3'-dimethoxy-[1,1'-biphenyl]-4-amine

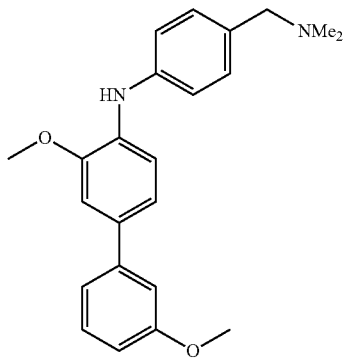 [SMILES: COc1cccc(-c2ccc(Nc3ccc(CN(C)C)cc3)c(OC)c2)c1]

Following General Procedure B, the product of preparation 2 (185 mg, 0.746 mmol) and 4-amino-N,N-dimethylbenzylamine (134 mg, 0.895 mmol) afforded the title product cjrb1901 (226 mg, 91%) as a yellow oil after purification on silica gel (MeOH:CH$_2$Cl$_2$ (1:9)).

$^1$H NMR (600 MHz, MeOD) δ=7.30 (1H, t, J 7.9) 7.29 (1H, d, J 7.9), 7.20 (2H, d, J 8.4), 7.18 (1H, d, J 2.0), 7.17 (1H, ddd, J 7.7, 1.7, 0.9), 7.14-7.12 (4H, m), 6.84 (1H, ddd, J 8.3, 2.6, 0.9), 3.94 (3H, s), 3.83 (3H, s), 3.47 (2H, s), 2.29 (6H, s), NH was not observed; $^{13}$C NMR (125 MHz, MeOD) δ=161.7, 151.0, 144.6, 144.2, 134.9, 133.8, 132.0, 130.9, 129.7, 120.4, 120.1, 118.9, 117.1, 113.4, 113.0, 110.9, 64.4, 58.4, 55.9, 44.9; LRMS (ESI+) 333.1 (M+H)$^+$; HRMS (ESI$^+$) [C$_{23}$H$_{27}$N$_2$O$_2$] requires 363.4810, found 363.4821.

Example 3: Synthesis of N-(4-((dimethylamino)methyl)phenyl)-2-fluoro-3,3'-dimethoxy-[1,1'-biphenyl]-4-amine

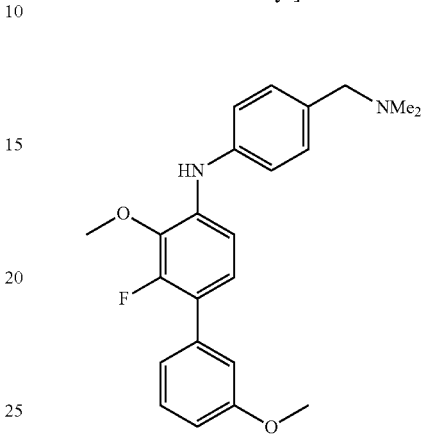

Following General Procedure B, the product of preparation 3 (110 mg, 0.414 mmol) and 4-amino-N,N-dimethylbenzylamine (75 mg, 0.497 mmol) afforded the title product (226 mg, 91%) as a yellow oil after purification on silica gel (MeOH:CH$_2$Cl$_2$ (1:9)).

$^1$H NMR (600 MHz, MeOD) δ=7.31 (1H, t, J 8.0), 7.24 (2H, d, J 8.3), 7.17 (2H, d, J 8.3), 7.08 (2H, td, J 8.6, 1.1), 7.05-7.03 (2H, m), 6.88 (1H, ddd, J 8.3, 2.6, 0.8), 3.91 (3H, d, J 0.9), 3.82 (3H, s), 3.49 (2H, s), 2.29 (6H, s), NH was not observed; $^{19}$F NMR (565 MHz, MeOD) δ=−137.7 (d, J 8.2); $^{13}$C NMR (125 MHz, MeOD) δ=161.3, 155.1 (d, J 243.2), 143.7, 139.4 9d, J 4.4), 138.8, 138.6 (d, J 14.3), 132.0, 131.0, 130.5, 125.6 (d, J 4.4), 122.6 9d, 12.1), 122.3 (d, J 3.3), 120.1, 115.6 (d, J 3.3), 113.6, 112.3 (d, J 2.2), 64.4, 61.8 (d, J 4.4), 55.9, 45.0; LRMS (ESI+) 381.3 (M+H)$^+$; HRMS (ESI$^+$) [C$_{23}$H$_{26}$FN$_2$O$_2$] requires 381.4714, found 381.4702.

Example 4: Synthesis of N-(4-((dimethylamino)methyl)phenyl)-4'-fluoro-3'-methoxy-[1,1'-biphenyl]-4-amine

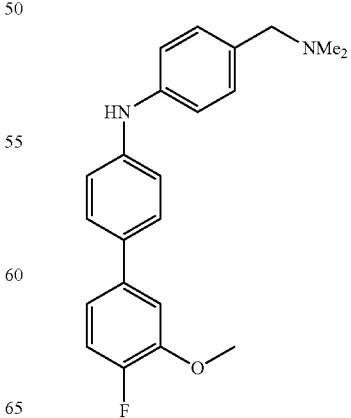

Following General Procedure B, the product of preparation 4 (110 mg, 0.429 mmol) and 4-amino-N,N-dimethylbenzylamine (77 mg, 0.515 mmol) afforded the title product (226 mg, 91%) as a yellow oil after purification on silica gel (MeOH:CH$_2$Cl$_2$ (3:22)).

$^1$H NMR (600 MHz, MeOD) δ=7.49 (2H, d, J 8.8), 7.23 (2H, d, J 8.8), 7.17 (3H, d, J 8.8), 7.12 (2H, d, J 7.0), 7.10 (4H, dd, J 7.0, 0.7), 3.93 (3H, s), 3.63 (2H, s), 2.41 (6H, s), NH was not observed; $^{19}$F NMR (565 MHz, MeOD) δ=−140.8 (q, J 8.2); $^{13}$C NMR (125 MHz, MeOD) δ=153.1 (d, J 245.4), 149.3 (d, J 11.0), 144.9 (d, J 148.6), 139.4 (d, J 4.4), 133.9, 132.3, 128.8, 128.6 (d, J 34.1), 127.7 (d, J 20.9), 119.8 (d, J 6.6), 118.9, 118.2, 117.1 (d, J 18.7), 113.2, 63.9, 56.9, 44.4; LRMS (ESI+) 351.3 (M+H)$^+$; HRMS (ESI$^+$) [C$_{22}$H$_{24}$FN$_2$O] requires 351.4454, found 351.4483.

Example 5: Synthesis of N-(4-((dimethylamino)methyl)phenyl)-3',4'-difluoro-5'-methoxy-[1,1'-biphenyl]-4-amine

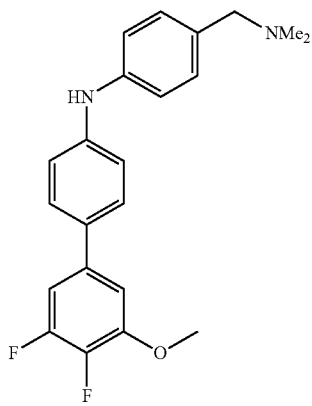 [SMILES: COc1cc(-c2ccc(Nc3ccc(CN(C)C)cc3)cc2)cc(F)c1F]

Following General Procedure B, the product of preparation 5 (110 mg, 0.429 mmol) and 4-amino-N,N-dimethylbenzylamine (77 mg, 0.515 mmol) afforded the title product (226 mg, 91%) as a yellow oil after purification on silica gel (MeOH:CH$_2$Cl$_2$ (3:22)).

$^1$H NMR (600 MHz, MeOD) δ=7.49 (2H, dt, J 8.9, 2.7), 7.23 (2H, dt, J 8.7, 2.6), 7.16 (2H, dt, J 8.9, 2.7), 7.13 (2H, dt, J 8.7, 2.6), 7.08 (1H, dt, J 7.1, 1.9), 7.04 (1H, ddd, J 11.5, 6.6, 2.2), 3.97 (3H, s), 3.58 (2H, s), 2.37 (6H, s), NH was not observed; $^{19}$F NMR (565 MHz, MeOD) δ=−140.6 (dd, J 19.6, 11.5), −166.2 (td, J 19.1, 6.0); $^{13}$C NMR (125 MHz, MeOD) δ=153.5 (dd, J 246.3, 9.9), 150.8 (dd, J 8.3, 3.9), 145.0 (d, J 80.3), 142.1 (dd, J 244.3, 15.4), 138.8 (dd, J 8.8, 4.1), 134.8, 132.4, 132.1, 129.2, 128.8, 118.6, 118.4, 108.0, 107.6 (d, J 18.7), 64.3, 57.4, 44.8; LRMS (ESI+) 351.3 (M+H)$^+$; HRMS (ESI$^+$) [C$_{22}$H$_{23}$F$_2$N$_2$O] requires 369.4358, found 369.4320.

Example 6: Synthesis of N-(4-((dimethylamino)methyl)phenyl)-3'-fluoro-5'-methoxy-[1,1'-biphenyl]-4-amine

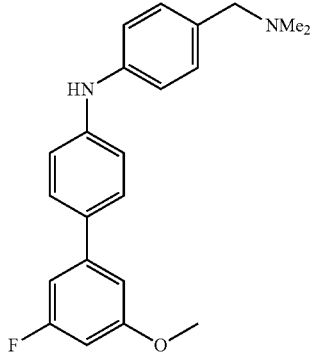 [SMILES: COc1cc(F)cc(-c2ccc(Nc3ccc(CN(C)C)cc3)cc2)c1]

Following General Procedure B, the product of preparation 6 (150 mg, 0.647 mmol) and 4-amino-N,N-dimethylbenzylamine (116 mg, 0.776 mmol) afforded the title product (184 mg, 81%) as a beige solid after purification on silica gel (MeOH:CH$_2$Cl$_2$ (3:22)).

$^1$H NMR (600 MHz, MeOD) δ=7.49 (2H, dt, J 8.8, 2.0), 7.21 (2H, dt, J 8.4, 2.0), 7.15 (2H, dt, J 8.6, 2.0), 7.12 (2H, dt, J 8.6, 2.0), 6.94 (1H, t, J 1.9), 6.89 (1H, ddd, J 9.9, 2.2, 1.5), 6.59 (1H, dt, J 10.7, 2.3), 3.84 (3H, s), 3.53 (2H, s), 2.33 (6H, s), NH was not observed; $^{19}$F NMR (565 MHz, MeOD) δ=−114.2 (d, J 10.2); $^{13}$C NMR (125 MHz, MeOD) δ=166.4, 164.8, 163.0 (d, J 12.1), 145.3 (d, J 6.6), 144.8, 134.8 (d, J 3.3), 132.1, 129.1, 128.9, 118.6, 118.4, 109.0 (d, J 2.2), 106.2 (d, J 23.1), 100.2 (d, J 26.4), 64.3, 56.2, 44.8; LRMS (ESI+) 351.3 (M+H)$^+$; HRMS (ESI$^+$) [C$_{22}$H$_{24}$FN$_2$O] requires 351.4454, found 351.4437.

Example 7: Synthesis of N-(4-((dimethylamino)methyl)phenyl)-3'-methoxy-5'-methyl-[1,1'-biphenyl]-4-amine

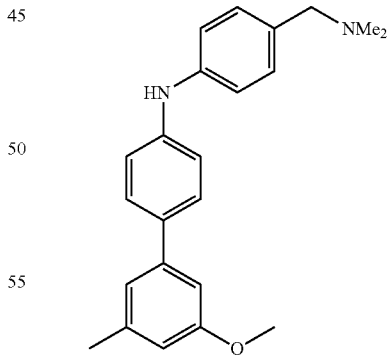

Following General Procedure B, the product of preparation 7 (150 mg, 0.644 mmol) and 4-amino-N,N-dimethylbenzylamine (112 mg, 0.774 mmol) afforded the title product (188 mg, 84%) as a yellow oil after purification on silica gel (MeOH:CH$_2$Cl$_2$ (3:22)).

$^1$H NMR (600 MHz, MeOD) δ=7.46 (2H, d, J 8.8), 7.20 (2H, d, J 8.4), 7.13 (2H, d, J 8.6), 7.10 (2H, d, J 8.4), 6.97 (1H, s), 6.89 (1H, s), 6.66 (1H, s), 3.80 (3H, s), 3.50 (2H, s), 2.35 (3H, s), 2.31 (6H, s), NH was not observed; $^{13}$C NMR (125 MHz, MeOD) δ=161.7, 145.0, 144.6, 143.7, 140.9, 134.5, 132.1, 128.9, 128.8, 120.8, 118.7, 118.2, 113.8, 110.3, 64.3, 55.8, 44.8, 21.8; LRMS (ESI+) 347.3 (M+H)$^+$; HRMS (ESI$^+$) [C$_{23}$H$_{27}$N$_2$O] requires 347.4280, found 347.4798.

Example 8: Synthesis of N-(3,5-dimethylphenyl)-2-fluoro-3,3'-dimethoxy-[1,1'-biphenyl]-4-amine

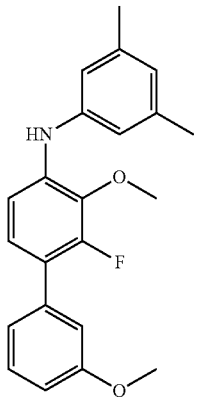 [SMILES: COc1cccc(-c2ccc(Nc3cc(C)cc(C)c3)c(OC)c2F)c1]

Following General Procedure B, the product of preparation 3 (100 mg, 0.376 mmol) and 3,5-dimethylaniline (56 µL, 0.451 mmol) afforded the title product (121 mg, 92%) as an off-white solid after purification on silica gel (EtOAc:pentane (1:19)).

$^1$H NMR (600 MHz, MeOD) δ=7.30 (1H, t, J 7.9), 7.06 (1H, ddd, J 7.7, 2.4, 1.3), 7.03 (1H, d, J 1.5), 7.02 (2H, q, J 8.6), 6.87 (1H, ddd, J 8.3, 2.6, 0.7), 6.81 (2H, s), 6.63 (1H, s), 3.91 (3H, s), 3.82 (3H, s), 2.27 (6H, s), NH was not observed; $^{19}$F NMR (565 MHz, MeOD) δ=−138.1 (d, J 6.1); $^{13}$C NMR (125 MHz, MeOD) δ=161.3, 155.0 (d, J 246.5), 143.7, 140.1, 139.9 (d, J 4.4), 138.9, 138.2 (d, J 14.3), 130.5, 125.6 (d, J 5.5), 124.7, 122.3 (d, J 3.3), 122.1 (d, 12.1), 118.8, 115.6 (d, J 3.3), 61.7 (d, J 5.5), 55.8, 21.6; LRMS (ESI+) 352.3 (M+H)$^+$; HRMS (ESI$^+$) [C$_{23}$H$_{23}$FNO$_2$] requires 352.4294, found 352.4261.

Example 9: Synthesis of N-(3,5-dimethylphenyl)-3'-methoxy-[1,1'-biphenyl]-4-amine

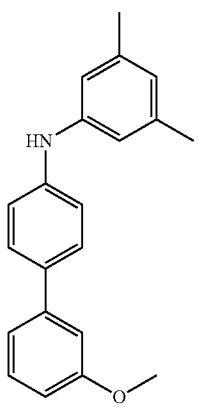 [SMILES: COc1cccc(-c2ccc(Nc3cc(C)cc(C)c3)cc2)c1]

Following General Procedure B, the product of preparation 1 (100 mg, 0.459 mmol) and 3,5-dimethylaniline (63 µL, 0.505 mmol) afforded the title product (133 mg, 96%) as a yellow solid after purification on silica gel (EtOAc:pentane (1:19)).

$^1$H NMR (600 MHz, MeOD) δ=7.48 (2H, d, J 8.8), 7.29 (1H, J 7.9), 7.14 (1H, ddd, J 7.7, 1.7, 0.9), 7.11 (2H, J 8.8), 7.10 (1H, ddd, J 2.4, 1.8, 0.7), 6.82 (1H, ddd, J 8.3, 2.6, 0.9), 6.75 (2H, s), 6.53 (1H, s), 3.83 (3H, s), 2.25 (6H, s), NH was not observed; $^{13}$C NMR (125 MHz, MeOD) δ=161.7, 145.3, 144.9, 144.1, 139.9, 133.7, 130.8, 128.8, 123.4, 119.9, 118.3, 116.8, 113.1, 112.8, 55.8, 21.7; LRMS(ESI+) 304.7 (M+H)$^+$; HRMS (ESI$^+$) [C$_{21}$H$_{22}$NO] requires 304.4130, found 304.4155.

Example 10: Synthesis of 3-((3'-methoxy-[1,1'-biphenyl]-4-yl)amino)-N,N,4-trimethylbenzamide

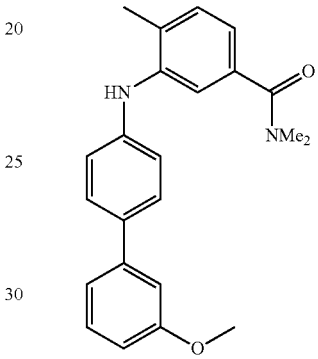

Following General Procedure B, the product of preparation 8 (183 mg, 0.758 mmol) and 3-bromo-N,N,4-trimethylbenzamide (116 mg, 0.583 mmol) afforded the title product (194 mg, 92%) as a yellow oil after purification on silica gel (MeOH:CH$_2$Cl$_2$ (3:47)).

$^1$H NMR (600 MHz, MeOD) δ=7.49 (2H, dt, J 8.8, 2.6), 7.29 (1H, t, J 8.1), 7.27 (1H, d, J 7.7), 7.24 (1H, d, J 1.8), 7.14 (1H, ddd, J 7.7, 1.7, 0.9), 7.10 (1H, dd, J 2.4, 1.7), 7.03 (2H, dt, J 8.6, 2.8), 6.94 (1H, dd, H 7.6, 1.7), 6.83 (1H, ddd, J 8.2, 2.5, 0.9), 3.83 (3H, s), 3.06 (3H, s), 3.02 (3H, s), 2.30 (3H, s), NH was not observed; $^{13}$C NMR (125 MHz, MeOD) δ=174.2, 161.7, 145.4, 143.9, 143.6, 135.6, 134.3, 132.5, 130.9, 128.9, 121.3, 119.9, 118.9, 118.7, 113.1, 113.0, 65.8, 40.3, 35.8, 18.3; LRMS (ESI+) 361.3 (M+H)$^+$; HRMS (ESI$^+$) [C$_{23}$H$_{25}$N$_2$O$_2$] requires 361.4650, found 361.4678.

Example 11: Synthesis of N-(5-((dimethylamino)methyl)-2-methylphenyl)-3'-methoxy-[1,1'-biphenyl]-4-amine

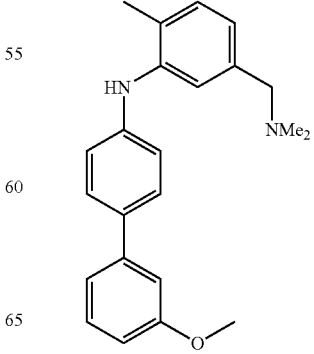

Following General Procedure B, the product of preparation 1 (40 mg, 0.183 mmol) and 5-((dimethylamino)methyl)-2-methylaniline (36 mg, 0.220 mmol) afforded the title product (44 mg, 69%) as a yellow oil after purification on silica gel (MeOH:CH$_2$Cl$_2$ (1:9)).

$^1$H NMR (600 MHz, MeOD) δ=7.45 (2H, dt, J 8.6, 2.7), 7.28 (1H, t, J 7.8), 7.19 (1H, d, J 2.0), 7.18 (1H, d, J 7.6), 7.13 (1H, dddd, J 7.6, 2.4, 1.7, 0.7), 7.08 (1H, t, J 2.4), 6.96 (2H, ddd, J 8.3, 2.7, 1.7), 6.88 (1H, dd, J 7.8, 2.0), 6.81 (1H, ddd, J 8.1, 2.7, 0.7), 3.82 (3H, s), 3.43 (2H, s), 2.25 (6H, s), 2.24 (3H, s), NH was not observed; $^{13}$C NMR (125 MHz, MeOD) δ=161.7, 146.3, 136.6, 133.4, 132.1, 130.8, 128.8, 125.0, 122.9, 119.8, 118.0, 113.0, 112.8, 64.8, 55.8, 45.3, 18.1; LRMS (ESI+) 347.3 (M+H)$^+$; HRMS (ESI$^+$) [C$_{23}$H$_{26}$N$_2$O] requires 347.4820, found 347.4856.

Example 12: Synthesis of N-(3-((2,6-dimethylmorpholino)methyl)phenyl)-3'-methoxy-[1,1'-biphenyl]-4-amine

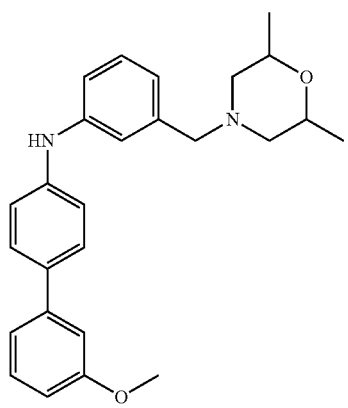

Following General Procedure B, the product of preparation 8 (110 mg, 0.553 mmol) and 4-(3-bromobenzyl)-2,6-dimethylmorpholine (171 mg, 0.605 mmol) afforded the title product (151 mg, 68%) as a yellow oil after purification on silica gel (MeOH:CH$_2$Cl$_2$ (3:47)).

$^1$H NMR (600 MHz, (CD$_3$)$_2$CO) δ=7.56 (2H, ddd, J 8.6, 2.8, 1.8), 7.52 (1H, brs), 7.32 (1H, t, J 7.9), 7.21-7.20 (2H, m), 7.20 (2H, d, J 8.6), 7.19 (1H, ddd, J 7.7, 1.7, 0.9), 7.15 (1H, dd, J 2.6, 1.7), 7.07 (1H, ddd, J 8.1, 2.2, 0.9), 6.86 (1H, dddd, J 10.8, 8.3, 2.6, 0.9), 6.87-6.84 (1H, m), 3.86 (3H, s), 3.60 (2H, dqd, J 10.1, 6.3, 2.1), 3.42 (2H, s), 2.73 (2H, dt, J 10.1, 1.8), 1.67 (2H, dd, J 11.3, 10.2), 1.06 (3H, s), 1.05 (3H, s); $^{13}$C NMR (125 MHz, (CD$_3$)$_2$CO) δ=161.3, 144.5, 144.4, 143.3, 140.6, 133.3, 130.7, 129.9, 128.6, 122.1, 119.4, 119.0, 118.1, 117.2, 112.9, 112.6, 72.4, 63.6, 60.5, 55.6, 19.6; LRMS (ESI+) 403.7 (M+H)$^+$; HRMS (ESI$^+$) [C$_{26}$H$_{31}$N$_2$O$_2$] requires 403.5460, found 403.5448.

Example 13: Synthesis of N-(3-((2,6-dimethylmorpholino)methyl)phenyl)-3'-methoxy-[1,1'-biphenyl]-4-amine

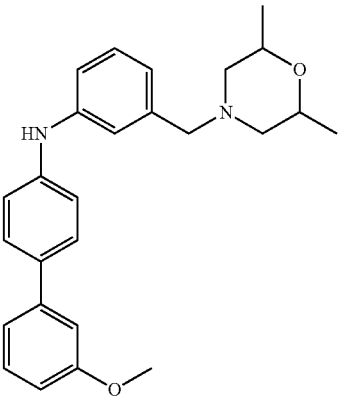 [SMILES: COc1cccc(-c2ccc(Nc3cccc(CN4CC(C)OC(C)C4)c3)cc2)c1]

Following General Procedure B, the product of preparation 8 (110 mg, 0.553 mmol) and 4-(3-bromobenzyl)-2,6-dimethylmorpholine (171 mg, 0.605 mmol) afforded the title product (151 mg, 68%) as a yellow oil after purification on silica gel (MeOH:CH$_2$Cl$_2$ (3:47)).

$^1$H NMR (600 MHz, (CD$_3$)$_2$CO) δ=7.56 (2H, ddd, J 8.6, 2.8, 1.8), 7.52 (1H, brs), 7.32 (1H, t, J 7.9), 7.21-7.20 (2H, m), 7.20 (2H, d, J 8.6), 7.19 (1H, ddd, J 7.7, 1.7, 0.9), 7.15 (1H, dd, J 2.6, 1.7), 7.07 (1H, ddd, J 8.1, 2.2, 0.9), 6.86 (1H, dddd, J 10.8, 8.3, 2.6, 0.9), 6.87-6.84 (1H, m), 3.86 (3H, s), 3.60 (2H, dqd, J 10.1, 6.3, 2.1), 3.42 (2H, s), 2.73 (2H, dt, J 10.1, 1.8), 1.67 (2H, dd, J 11.3, 10.2), 1.06 (3H, s), 1.05 (3H, s); $^{13}$C NMR (125 MHz, (CD$_3$)$_2$CO) δ=161.3, 144.5, 144.4, 143.3, 140.6, 133.3, 130.7, 129.9, 128.6, 122.1, 119.4, 119.0, 118.1, 117.2, 112.9, 112.6, 72.4, 63.6, 60.5, 55.6, 19.6; LRMS (ESI+) 403.7 (M+H)$^+$;
HRMS (ESI$^+$) [C$_{26}$H$_{31}$N$_2$O$_2$] requires 403.5460, found 403.5448.

Example 14: Synthesis of N-(4-((dimethylamino)methyl)phenyl)-2-methoxy-6-(3-methoxyphenyl)pyridin-3-amine

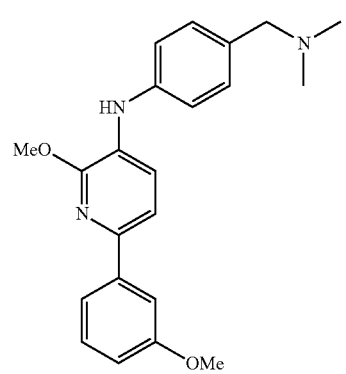 [SMILES: COc1cccc(-c2ccc(Nc3ccc(CN(C)C)cc3)c(OC)n2)c1]

Following General Procedure B, 1-(4-bromophenyl)-N,N-dimethylmethanamine (56 mg, 0.261 mmol) and the product of preparation 9 (50 mg, 0.217 mmol) afforded the title product (67 mg, 71%) as a yellow oil after purification on silica gel (MeOH:CH$_2$Cl$_2$ (1:9)).

¹H NMR (600 MHz, MeOD) δ=7.59 (1H, dd, J 2.7, 1.5) 7.57 (1H, dt, J 7.7, 1.4) 7.53 (1H, d, J 8.1 Hz), 734 (1H, d, J 8.1 Hz), 7.30 (1H, t, J 7.9) 7.25 (2H, d, J 8.3), 7.15 (2H, d, J 8.3), 6.87 (1H, ddd, J 8.2, 2.6, 0.7), 4.11 (3H, s), 3.85 (3H, s), 3.50 (2H, s), 2.31 (6H, s), NH was not observed; ¹³C NMR (125 MHz, MeOD) δ=161.6, 154.8, 145.1, 143.5, 142.1, 132.1, 130.6, 130.4, 128.6, 121.9, 119.8, 119.3, 114.3, 114.1, 112.5, 64.3, 55.8, 53.9, 44.9; LRMS (ESI+) 364.7 (M+H)⁺; HRMS (ESI⁺) [C₂₂H₂₆N₃O₂] requires 364.4690, found 364.4681.

Example 15: Synthesis of N-(3-((dimethylamino)methyl)phenyl)-2-methoxy-6-(3-methoxyphenyl)pyridin-3-amine

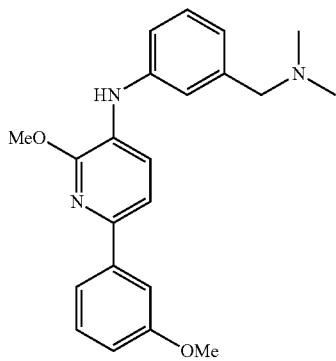 [SMILES: COc1cccc(-c2ccc(Nc3cccc(CN(C)C)c3)c(OC)n2)c1]

Following General Procedure B, 1-(3-bromophenyl)-N,N-dimethylmethanamine (56 mg, 0.261 mmol) and the product of preparation 9 (50 mg, 0.217 mmol) afforded the title product (64 mg, 68%) as a yellow oil after purification on silica gel (MeOH:CH₂Cl₂ (1:9)).

¹H NMR (600 MHz, MeOD) δ=7.59 (1H, dd, J 2.4, 1.5), 7.45 (1H, d, J 8.1), 7.42 (1H, d, J 8.1), 7.31 (2H, t, J 8.1), 7.15 (1H, dd, J 8.8, 7.6), 7.11-7.09 (2H, m), 6.88 (1H, d, J 8.3), 6.86 (1H, ddd, J 5.4, 2.6, 0.9), 3.99 (3H, s), 3.74 (3H, s), 3.36 (2H, s), 2.17 (6H, s), NH was not observed; ¹³C NMR (125 MHz, MeOD) δ=161.6, 154.6, 145.0, 143.9, 142.1, 139.6, 130.6, 130.4, 128.7, 123.9, 121.8, 123.9, 120.9, 119.3, 119.2, 114.3, 114.1, 112.5, 65.0, 55.8, 53.9, 45.3; LRMS (ESI+) 364.7 (M+H)⁺; HRMS (ESI⁺) [C₂₂H₂₆N₃O₂] requires 364.4690, found 364.4678.

Example 16: Synthesis of N-(4-((dimethylamino)methyl)phenyl)-6-(3-methoxyphenyl)pyridin-3-amine

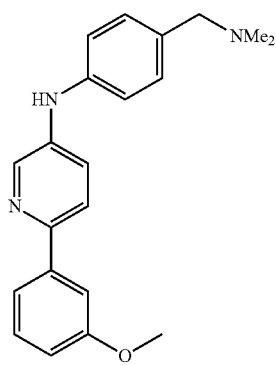

Following General Procedure B, the product of preparation 10 (250 mg, 1.25 mmol) and 1-(4-bromophenyl)-N,N-dimethylmethanamine (320 mg, 1.50 mmol) afforded the title product (391 mg, 94%) as a dark yellow oil after purification on silica gel (MeOH:CH₂Cl₂ (1:9 to 1:4)).

¹H NMR (600 MHz, MeOD) δ=8.34 (1H, dd, J 2.8, 0.5), 7.67 (1H, ddd, J 8.6, 2.0, 0.6), 7.58 (1H, dt, J 8.8, 2.9), 7.44 (1H, dd, J 2.6, 1.7), 7.40 (1H, dt, J 7.9, 1.1), 7.33 (1H, t, J 7.9), 7.24 (2H, d, J 8.3), 7.12 (2H, d, J 8.4), 6.91 (1H, dd, J 8.2, 2.7), 3.85 (3H, s), 3.44 (2H, s), 2.26 (6H, s), NH was not observed; ¹³C NMR (125 MHz, MeOD) δ=161.7, 149.8, 143.3, 142.0, 141.5, 139.4, 132.1, 131.3, 130.9, 124.9, 122.9, 119.8, 119.1, 114.9, 112.8, 64.4, 55.9, 55.8, 45.1; LRMS (ESI+) 334.3 (M+H)⁺; HRMS (ESI⁺) [C₂₁H₂₄N₃O] requires 334.3430, found 334.3411.

Example 17: Synthesis of 3-((3'-methoxy-[1,1'-biphenyl]-4-yl)amino)-N-(piperidin-4-ylmethyl)benzamide

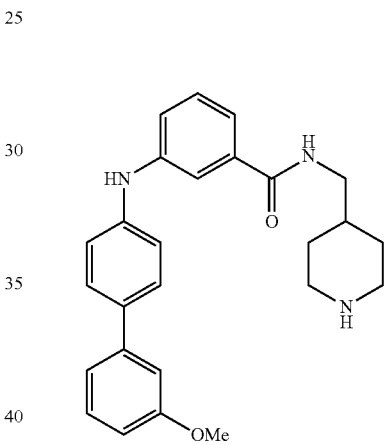

Following General Procedure B, the product of preparation 8 (85 mg, 0.427 mmol) and tert-butyl 4-((3-bromobenzamido)methyl)piperidine-1-carboxylate (220 mg, 0.555 mmol) afforded the Boc protected title product (65 mg, 30%) as a yellow oil after purification on silica gel (MeOH:CH₂Cl₂ (1:4)). A solution of the Boc protected title product (50 mg, 0.097 mmol, 1.0 eq.) in CH₂Cl₂ (2 mL) was treated with TFA (50 μL, 0.653 mmol, 6.7 eq.), and the resulting solution stirred for 18 h. The solvent was removed in vacuo and the crude residue purified by column chromatography on silica gel (Et₃N:MeOH:CH₂Cl₂ (1:20:79 to 5:20:75)) to afford the title product as a dark yellow oil (17 mg, 42%).

¹H NMR (600 MHz, MeOD) δ=7.58 (1H, t, J 2.0), 7.53 (2H, dt, J 8.6, 2.6), 7.32 (2H, dt, J 9.9, 7.9), 7.26-7.25 (1H, m), 7.25 (1H, ddd, J 5.3, 2.4, 1.1), 7.20 (2H, dd, J 8.4, 2.9, 1.8), 7.16 (1H, dd, J 7.7, 0.9), 7.11 (1H, t, J 2.4), 6.85 (1H, ddd, J 8.2, 2.5, 0.9), 3.84 (3H, s), 3.41 (2H, app d, J 12.5), 3.34 (2H, d, J 6.6), 2.99 (2H, app t, J 12.4), 1.99 (3H, app d, J 12.8), 1.52-1.48 (2H, m), NHs were not observed; ¹³C NMR (125 MHz, MeOD) δ=171.1, 161.7, 145.8, 144.1, 143.8, 136.8, 134.8, 136.8, 134.8, 130.9, 130.6, 128.9, 121.3, 119.9, 119.5, 119.2, 116.6, 113.2, 113.0, 55.9, 45.6, 45.4, 35.7, 29.7; LRMS (ESI+) 416.8 (M+H)⁺; HRMS (ESI⁺) [C₂₆H₂₉N₃O₂] requires 416.5450, found 416.5411.

Example 18: Synthesis of N-(4-((dimethylamino)methyl)phenyl)-3'-methoxy-4'-methyl-[1,1'-biphenyl]-4-amine

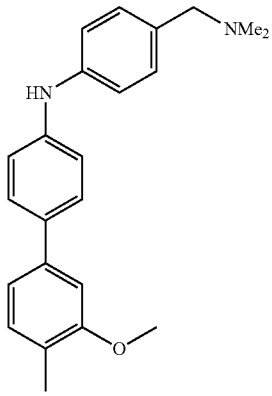 [SMILES: COc1cc(-c2ccc(Nc3ccc(CN(C)C)cc3)cc2)ccc1C]

Following General Procedure B, the product of preparation 11 (150 mg, 0.704 mmol) and 1-(4-bromophenyl)-N,N-dimethylmethanamine (180 mg, 0.845 mmol) afforded the title product (167 mg, 69%) as a yellow oil after purification on silica gel (MeOH:CH$_2$Cl$_2$ (3:17)).

$^1$H NMR (600 MHz, MeOD) δ=7.47 (2H, dt, J 8.8, 2.7), 7.17 (2H, dd, J 6.6, 2.2), 7.13 (2H, dt, J 8.8, 2.9), 7.11-7.09 (1H, m), 7.08 (2H, dd, J 6.6, 2.0), 7.04 (1H, d, J 1.5), 7.02 (1H, dd, J 7.3, 1.7), 3.84 (3H, s), 3.47 (2H, s), 2.29 (6H, s), 2.18 (3H, s); $^{13}$C NMR (125 MHz, MeOD) δ=159.5, 145.1, 144.2, 141.4, 134.7, 132.1, 131.9, 128.7, 125.8, 119.4, 118.8, 109.2, 64.2, 44.7, 16.2; LRMS (ESI+) 347.3 (M+H)$^+$; HRMS (ESI$^+$) [C$_{23}$H$_{27}$N$_2$O] requires 347.4820, found 347.4832.

Example 19: Synthesis of N-((1-benzylpiperidin-4-yl)methyl)-4-((3'-methoxy-[1,1'-biphenyl]-4-yl)amino)benzamide

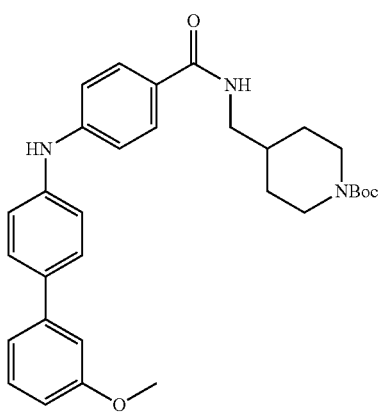 [SMILES: COc1cccc(-c2ccc(Nc3ccc(C(=O)NCC4CCN(C(=O)OC(C)(C)C)CC4)cc3)cc2)c1]

Following General Procedure B, the product of preparation 1 (55 mg, 0.250 mmol) and tert-butyl 4-((4-aminobenzamido)methyl)piperidine-1-carboxylate (100 mg, 0.300 mmol) afforded the title product (102 mg, 79%) as a yellow oil after purification on silica gel (MeOH:CH$_2$Cl$_2$ (1:4)).

$^1$H NMR (400 MHz, MeOD) δ=7.76 (2H, dt, 8.9, 2.7), 7.56 (2H, dt, J 8.8, 2.7), 7.35 (1H, t, J 8.0), 7.25 (2H, dt, J 9.4, 2.7), 7.19 (1H, ddd, J 7.6, 1.7, 0.9), 7.15-7.12 (3H, m), 6.86 (1H, ddd, J 8.2, 2.5, 1.0), 4.11 (2H, br dt, J 13.3, 3.7), 3.86 (3H, s), 3.25 (2H, d, J 6.7), 2.75 (2H, brs), 1.87-1.79 (1H, m), 1.73 (2H, brd, J 13.3), 1.45 (9H, s), 1.13 (2H, brqd, J 12.0, 4.2), NH were not observed; $^{13}$C NMR (75 MHz, MeOD) δ=170.3, 161.7, 156.7, 149.0, 143.7, 143.2, 135.7, 130.9, 130.0, 129.0, 125.8, 120.4, 120.0, 161.1, 113.3, 113.2, 81.1, 55.8, 46.3, 30.8, 28.8; LRMS (ESI+) 516.8 (M+H)$^+$; HRMS (ESI$^+$) [C$_{31}$H$_{38}$N$_3$O$_4$] requires 516.6620, found 516.6603.

Example 20: Synthesis of 4-((3'-methoxy-[1,1'-biphenyl]-4-yl)amino)-N-(piperidin-4-ylmethyl)benzamide

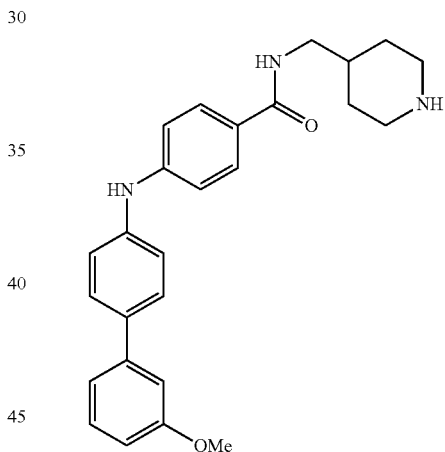

A solution of example 19 (125 mg, 0.247 mmol, 1.0 eq.) in CH$_2$Cl$_2$ (5 mL) was treated with TFA (50 µL, 2.61 mmol, 10.5 eq.), and the resulting solution stirred for 18 h. The solvent was removed in vacuo afford the title compound as a yellow oil (82 mg, 80%), which did not require any further purification.

$^1$H NMR (400 MHz, MeOD) δ=7.73 (2H, dt, J 8.7, 2.6), 7.57 (2H, dt, J 8.8, 2.8), 7.32 (1H, t, J 8.1), 7.24 (2H, dt, J 8.8, 2.8), 7.17 (1H, ddd, J 7.7, 1.7, 0.9), 7.12 (2H, dt, J 8.8, 2.8), 7.13 (1H, s), 6.87 (1H, ddd, J 8.2, 2.6, 1.0), 3.85 (3H, s), 3.42 (2H, dt, J 12.6, 3.5), 3.34 (2H, d, J 6.5), 2.98 (2H, td, J 13.0, 2.8), 2.02-1.94 (3H, m), 1.50 (2H, dt, J 14.2, 3.4), NHs were not observed; $^{13}$C NMR (75 MHz, MeOD) δ=149.1, 143.7, 143.1, 135.7, 131.0, 130.1, 129.0, 125.5, 120.5, 120.0, 116.0, 113.3, 113.2, 55.8, 45.5, 45.1, 35.8, 28.0; LRMS (ESI+) 416.8 (M+H)$^+$; HRMS (ESI$^+$) [C$_{26}$H$_{29}$N$_3$O$_2$] requires 416.5450, found 416.5423.

Example 21: Synthesis of 4-((3'-methoxy-[1,1'-biphenyl]-4-yl)amino)-N-((1-methylpiperidin-4-yl)methyl)benzamide

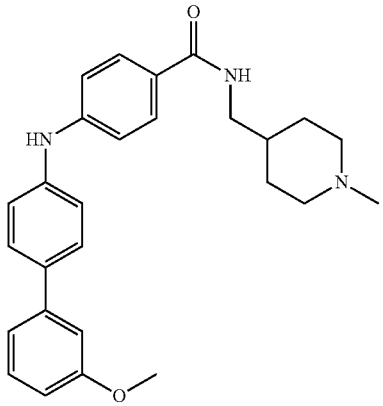 [SMILES: COc1cccc(-c2ccc(Nc3ccc(C(=O)NCC4CCN(C)CC4)cc3)cc2)c1]

Following General Procedure B, the product of preparation 1 (112 mg, 0.459 mmol) and 4-amino-N-((1-methylpiperidin-4-yl)methyl)benzamide (135 mg, 0.550 mmol) afforded the title product (159 mg, 83%) as a yellow oil after purification on silica gel (Et$_3$N:MeOH:CH$_2$Cl$_2$ (0:1:9 to 1:15:84)).

$^1$H NMR (400 MHz, MeOD) δ=7.56 (1H, t, J 2.2), 7.53 (2H, dt, J 8.7, 2.7), 7.30 (2H, ddd, J 7.8, 4.1, 3.2), 7.25 (2H, ddd, J 8.6, 2.7, 1.2), 7.19 (2H, ddd, J 8.9, 2.9, 2.1), 7.16 (1H, ddd, J 7.7, 1.7, 1.0), 7.11 (1H, dd, J 2.4, 1.7), 6.85 (1H, ddd, J 8.2, 2.5, 0.9), 3.84 (3H, s), 3.27 (2H, d, J 6.8), 2.92 (2H, br d, J 12.3), 2.28 (3H, s), 2.04 (2H, brt, J 12.0), 1.78 (2H, brd, J 13.8), 1.69-1.64 (1H, m), 1.34 (2H, qd, J 12.2, 3.5); NHs were not observed; $^{13}$C NMR (75 MHz, MeOD) δ=171.0, 161.7, 145.8, 144.2, 143.9, 137.2, 134.7, 130.9, 130.5, 128.9, 121.1, 120.0, 119.5, 119.1, 116.8, 113.2, 113.0, 56.5, 55.8, 46.4 (×2), 36.7, 30.8; LRMS (ESI+) 430.5 (M+H)$^+$; HRMS (ESI$^+$) [C$_{27}$H$_{32}$N$_3$O$_2$] requires 430.5720, found 430.5736.

Example 22: Synthesis of 4-((3',4'-difluoro-5'-methoxy-[1,1'-biphenyl]-4-yl)amino)-N-((1-methylpiperidin-4-yl)methyl)benzamide

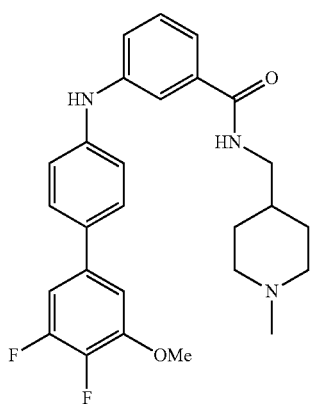 [SMILES: COc1cc(-c2ccc(Nc3cccc(C(=O)NCC4CCN(C)CC4)c3)cc2)cc(F)c1F]

Following General Procedure B, the product of preparation 5 (90 mg, 0.381 mmol) and 4-amino-N-((1-methylpiperidin-4-yl)methyl)benzamide (113 mg, 0.457 mmol) afforded the title product (137 mg, 80%) as a beige solid after purification on silica gel ((Et$_3$N:MeOH:CH$_2$Cl$_2$ (0:1:9 to 1:15:84)).

$^1$H NMR (600 MHz, MeOD) δ=7.57 (1H, t, J 1.9), 7.50 (2H, ddd, J 8.6, 2.8, 2.0), 7.32 (1H, t, J 7.9), 7.27 (1H, dt, J 6.2, 1.3), 7.25 (1H, ddd, J 5.7, 2.4, 1.1), 7.19 (2H, ddd, J 8.6, 2.8, 2.0), 7.07 (1H, dt, J 7.0, 1.8), 7.03 (1H, ddd, J 11.4, 6.6, 2.2), 3.96 (3H, s), 3.27 (2H, d, J 6.8), 2.92 (2H, brd, J 12.1), 2.31 (3H, s), 2.10 (2H, td, J 11.9, 1.8), 1.79 (2H, brd, J 12.7), 1.72-1.64 (1H, m), 1.35 (2H, tdd, J 13.0, 3.9, 1.5), NH were not observed; $^{19}$F NMR (565 MHz, CDCl$_3$) δ=−140.5 (dd, J 22.5, 10.2), −166.0 (dt, J 18.4, 6.1); $^{13}$C NMR (125 MHz, MeOD) δ=170.9, 152.7 (dd, J 244.3, 9.9), 150.8 (dd, J 7.3, 3.3), 145.1 (d, J 93.5), 141.3 (dd, J 246.3, 14.3), 138.7 (dd, J 7.7, 4.4), 137.2, 132.8, 130.6, 128.9, 121.5, 119.8, 118.8, 117.1, 108.1 (d, J 2.2), 107.7 (d, J 18.7), 57.4, 56.4, 46.3, 36.6, 30.7; LRMS (ESI+) 466.7 (M+H)$^+$; HRMS (ESI$^+$) [C$_{27}$H$_{30}$F$_2$N$_3$O$_2$] requires 466.5528, found 466.5654.

Example 23: Synthesis of N-((1-benzylpiperidin-4-yl)methyl)-4-((3'-methoxy-[1,1'-biphenyl]-4-yl)amino)benzamide

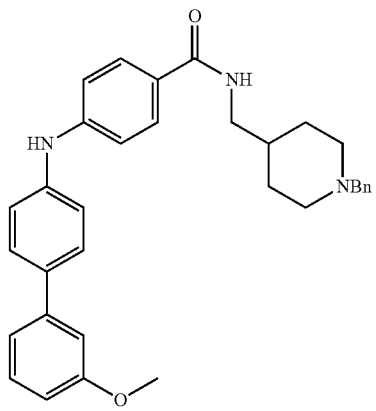 [SMILES: COc1cccc(-c2ccc(Nc3ccc(C(=O)NCC4CCN(Cc5ccccc5)CC4)cc3)cc2)c1]

Following General Procedure B, the product of preparation 1 (112 mg, 0.516 mmol) and 4-amino-N-((1-benzylpiperidin-4-yl)methyl)benzamide (200 mg, 0.619 mmol) afforded the title product (191 mg, 73%) as a yellow oil after purification on silica gel (MeOH:CH$_2$Cl$_2$ (1:4)).

$^1$H NMR (600 MHz, MeOD) δ=7.72 (2H, dt, 9.0, 2.7), 7.56 (2H, dt, J 8.8, 2.7), 7.35-7.25 (4H, m), 7.30 (2H, d, J 9.1), 7.24 (2H, dt, J 8.8, 2.7), 7.17 (1H, ddd, J 7.8, 1.7, 0.7), 7.12 (1H, d, J 2.4), 7.11 (2H, dt, J 8.8, 2.0), 6.86 (1H, ddd, J 8.2, 2.6, 1.0), 3.85 (3H, s), 3.61 (2H, s), 3.26 (2H, d, J 6.6), 2.99 (2H, br d, J 11.5), 2.16 (2H, br t, J 11.7), 1.78 (2H, br d, J 13.2), 1.73-1.70 (1H, m), 1.35 (2H, brqd, J 12.5, 3.9), NHs were not observed; $^{13}$C NMR (125 MHz, MeOD) δ=170.2, 161.7, 148.9, 143.6, 143.1, 137.6, 135.6, 131.2, 130.9, 130.0, 128.9, 128.8, 125.8, 120.4, 120.0, 116.1, 113.3, 113.2, 64.1, 55.8, 54.4, 46.3, 37.3, 30.5; LRMS (ESI+) 506.7 (M+H)$^+$; HRMS (ESI$^+$) [C$_{35}$H$_{36}$N$_3$O$_2$] requires 506.6700, found 506.6692.

Biological Activity
Protein Expression and Purification

For SPR assays pGEX-KRAS(G12V) plasmid was transformed into *E. coli* C41(DE3). Bacterial cells were cultured at 37° C. to an OD$_{600}$ of 0.6 and induced with IPTG (final 0.1 mM) at 18° C. over night. The GST fusion proteins were extracted from bacteria pellets after cell disruption in 140 mM NaCl, 2.7 mM KCl, 10 mM NaH$_2$PO$_4$, 1.8 mM KH$_2$PO$_4$, 1 mM EDTA, 2 mM MgCl$_2$ pH 7.4 and purified by glutathione-sepharose column chromatography (GE Healthcare), eluting with 50 mM Tris-HCl pH8.0, 10 mM reduced glutathione, 1 mM DTT, 2 mM MgCl$_2$. The eluted proteins were dialysed against 50 mM Tris-HCl pH8.0, 1 mM DTT, 2 mM MgCl$_2$ and concentrated to 10 mg/ml using a Biomax-30 ULTRAFREE-15 centrifugal filter device (Millipore). Purified KRAS protein was loaded with GPPNHP as described elsewhere (Pacold et al., 2000). Loaded protein was then purified by gel filtration on a HiLoad Superdex-75 HR column (GE Healthcare) in 1×PBS pH7.4, 5 mM MgCl$_2$ and concentrated for storage. Protocol for KRas small-molecule screening and affinity measurements by SPR
Protein Immobilization To a previously immobilized CM5 chip (GE Healthcare BR-1005-30) with anti GST antibody via amine coupling method, GST in channel 1 and GST-human KRas166 (G12V) GPPNHP in channel 2 were immobilised. GST was immobilised between 2,000 and 5,000 Response units. KRAS166 (G12V) was immobilized between 10,000 to 15,000 Response Units.

Compound Screening

In a 96 well plate, compounds were diluted in 25 mM, 100 mM NaCl, 5 mM MgCl$_2$ and 5% DMSO Buffer to a final concentration of 100 uM. DCAI was used as positive control. Experiment also included a solvent correction curve for 5% DMSO. Screening and evaluation of the protein immobilization and the compounds screening was done accordingly to the BIACORE T200 control and evaluation software.

Calculations for how many response units are required for a 1:1 ratio of compound/protein interaction are shown below.

Protein immobilisation: 10,000 RU; average fragment 300 Da in size.

$$R_{max}=(MWA/MWL) \times RL \times SM$$

MWA is the molecular weight of the analyte in Da
MWL is the molecular weight of the ligand in Da
RL is the immobilization level in RU
SM is the molar stoichiometry (assume 1:1)

Rmax=300/47,500×10,000×1
Rmax=63 RU.

BRET2 Cell Assay 650,000 HEK293T were seeded in each well of a 6 well plate. 24 hours later, cells were transfected with an appropriated BRET-based RAS biosensor (i.e. RAS-effector) using Lipofectamine 2000 transfection reagent (ThermoFisher). Cells were detached 24 hours later and washed with PBS and seeded in a white 96 well plate (clear bottom, PerkinElmer, cat #6005181) in OptiMEM no phenol red medium (Life Technologies) complemented with 4% FBS. Cells were left for 4 hours at 37° C. before adding compounds. Stock compounds were held at 10 mM in 100% DMSO and diluted in OptiMEM no red phenol+4% FBS to reach 10× the final concentration (2% DMSO for each concentration). The final concentrations in the cells were 0, 5, 10 and 20 μM (therefore the intermediate 10× concentrations were 0, 50, 100 and 200 μM. 10 μL of 10× compounds were added in each well of the 96 well plate to 0, 5, 10 and 20 μM final concentrations (with final 0.2% DMSO each). Quadruplicates were performed for each point. Cells were left for an additional 20 hours at 37° C. before the BRET2 signal reading directly after addition of Coelenterazine 400a substrate (10 μM final) to cells (Cayman Chemicals, cat #16157). BRET2 reading was carried out on an Envision instrument (2103 Multilabel Reader, PerkinElmer) with the BRET2 Dual Emission optical module (515 nm±30 and 410 nm±80; PerkinElmer).

Cell Viability Assay Protocols

DLD1 cells (ATCC CCL-221) are cultured in RPMI-1640 medium plus 10% foetal calf serum and 2 mM L-glutamine at 37° C. 5% CO$_2$. Cells are plated onto white clear bottom 96-well plates (5000 cells/well in 200 μl media) and left to adhere overnight at 37° C., 5% CO$_2$. Next day, test compound (1 μl at 200× concentration in 100% DMSO) is added to give final test compound concentration 1× in 0.5% DMSO. After 72 h of incubation at 37° C. 5% CO$_2$, 20 μl CellTiter-Glo reagent (Promega G7572) is added into each well. Plates are incubated at room temperature with shaking for 30 min and then luminescence is read using a PheraStar plate reader. The concentration of compounds that decrease cell viability by 50% is calculated from dose response curves generated using Dotmatics data analysis software Results

TABLE 1

SPR, BRET and Cell Viability

| Example No. | Chemical Structure | SPR | Viability data IC$^{50}$(DLD-1) 72 h | BRET RASG12D/CRAF FL % Inhibition (10 uM) |
|---|---|---|---|---|
| 1 | 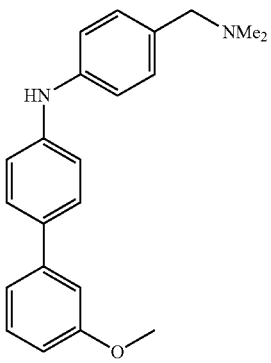 [SMILES: COc1cccc(-c2ccc(Nc3ccc(CN(C)C)cc3)cc2)c1] | 230 | 5.3 μM | 24% |

TABLE 1-continued

SPR, BRET and Cell Viability

| Example No. | Chemical Structure | SPR | Viability data IC$^{50}$(DLD-1) 72 h | BRET RASG12D/CRAF FL % Inhibition (10 uM) |
|---|---|---|---|---|
| 2 | 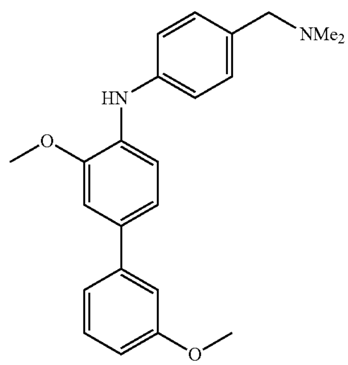 [SMILES: COc1cccc(-c2ccc(Nc3ccc(CN(C)C)cc3)c(OC)c2)c1] | 233 | 7.2 μM | 18% |
| 3 | 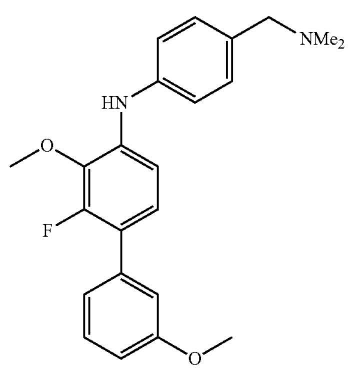 [SMILES: COc1cccc(-c2ccc(Nc3ccc(CN(C)C)cc3)c(OC)c2F)c1] | 177 | 4.5 μM | 26% |
| 4 | 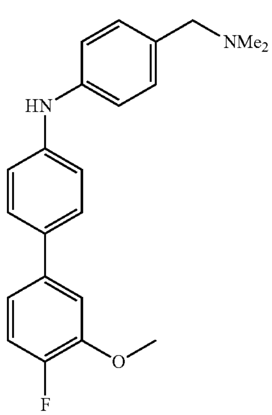 [SMILES: COc1cc(-c2ccc(Nc3ccc(CN(C)C)cc3)cc2)ccc1F] | 80 | | 24% |

TABLE 1-continued
SPR, BRET and Cell Viability
| Example No. | Chemical Structure | SPR | Viability data IC$^{50}$(DLD-1) 72 h | BRET RASG12D/CRAF FL % Inhibition (10 uM) |
|---|---|---|---|---|
| 5 | 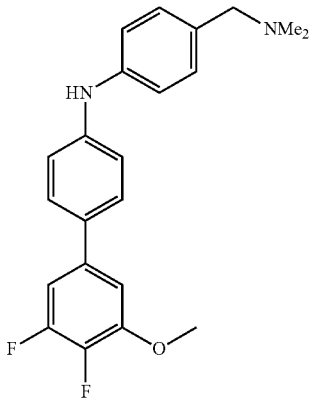 [SMILES: COc1cc(-c2ccc(Nc3ccc(CN(C)C)cc3)cc2)cc(F)c1F] | | 127 | 33% |
| 6 | 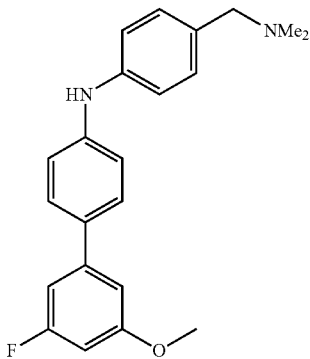 [SMILES: COc1cc(F)cc(-c2ccc(Nc3ccc(CN(C)C)cc3)cc2)c1] | | 245 | 22% |
| 7 | 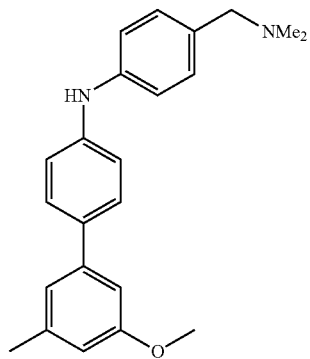 [SMILES: COc1cc(C)cc(-c2ccc(Nc3ccc(CN(C)C)cc3)cc2)c1] | | 264 | 6% |

TABLE 1-continued

SPR, BRET and Cell Viability

| Example No. | Chemical Structure | SPR | Viability data IC$^{50}$(DLD-1) 72 h | BRET RASG12D/CRAF FL % Inhibition (10 uM) |
|---|---|---|---|---|
| 8 | 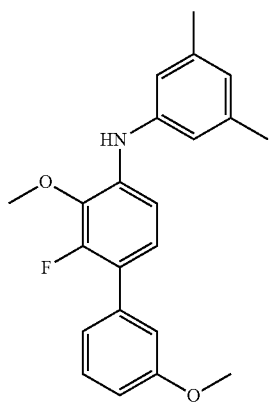 | | 30 | 0% |
| 9 | 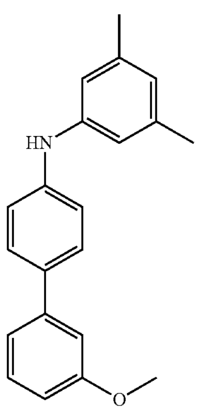 [SMILES: COc1cccc(-c2ccc(Nc3cc(C)cc(C)c3)cc2)c1] | | 28 | 2% |
| 10 | 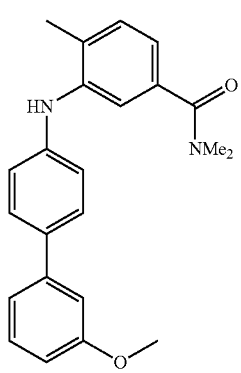 [SMILES: COc1cccc(-c2ccc(Nc3cc(C(=O)N(C)C)ccc3C)cc2)c1] | | 28 | 0% |

TABLE 1-continued

SPR, BRET and Cell Viability

| Example No. | Chemical Structure | SPR | Viability data IC$^{50}$(DLD-1) 72 h | BRET RASG12D/CRAF FL % Inhibition (10 uM) |
|---|---|---|---|---|
| 11 | 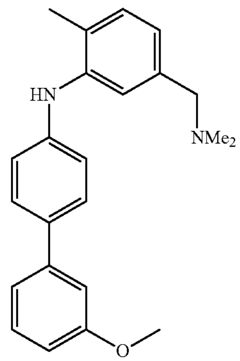 [SMILES: COc1cccc(-c2ccc(Nc3cc(CN(C)C)ccc3C)cc2)c1] | | 69 | 1% |
| 12 | 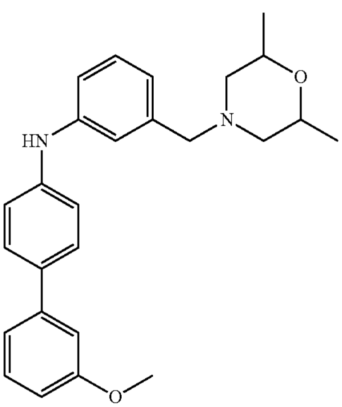 [SMILES: COc1cccc(-c2ccc(Nc3cccc(CN4CC(C)OC(C)C4)c3)cc2)c1] | | 55 | 0% |
| 13 | 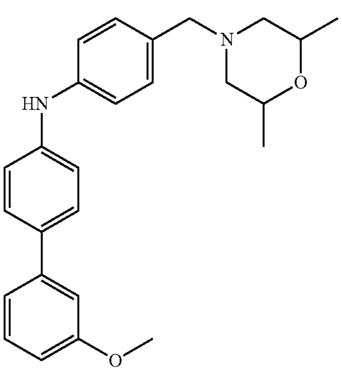 [SMILES: COc1cccc(-c2ccc(Nc3ccc(CN4CC(C)OC(C)C4)cc3)cc2)c1] | | 43 | 9% |
| 14 | 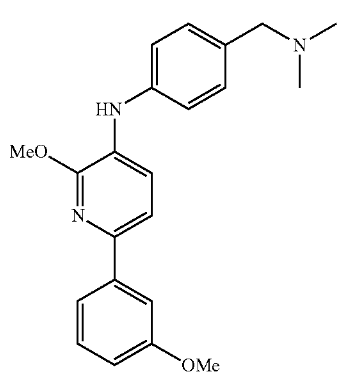 [SMILES: COc1cccc(-c2ccc(Nc3ccc(CN(C)C)cc3)c(OC)n2)c1] | | 152 | 42% |

TABLE 1-continued

SPR, BRET and Cell Viability

| Example No. | Chemical Structure | SPR Viability data IC$^{50}$(DLD-1) 72 h | BRET RASG12D/CRAF FL % Inhibition (10 uM) |
|---|---|---|---|
| 15 | 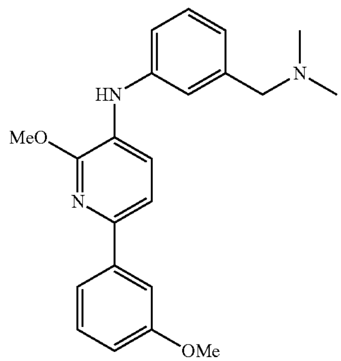 [SMILES: COc1cccc(-c2ccc(Nc3cccc(CN(C)C)c3)c(OC)n2)c1] | 84 | 35% |
| 16 | 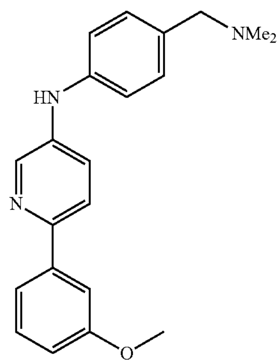 [SMILES: COc1cccc(-c2ccc(Nc3ccc(CN(C)C)cc3)cn2)c1] | 209 | 0% |
| 17 | 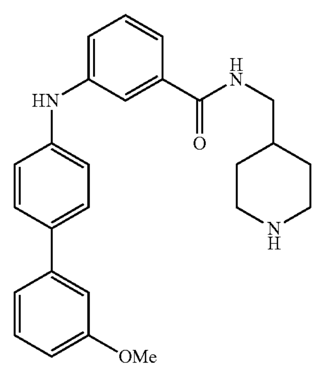 [SMILES: COc1cccc(-c2ccc(Nc3cccc(C(=O)NCC4CCNCC4)c3)cc2)c1] | 396 | |
| 18 | 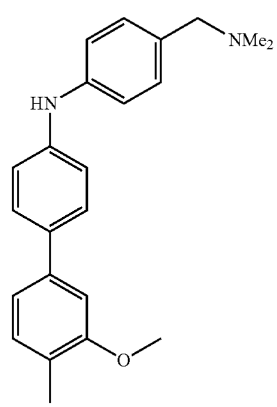 [SMILES: COc1cc(-c2ccc(Nc3ccc(CN(C)C)cc3)cc2)ccc1C] | 119 | 13% |

TABLE 1-continued
SPR, BRET and Cell Viability
| Example No. | Chemical Structure | SPR | Viability data IC$^{50}$(DLD-1) 72 h | BRET RASG12D/CRAF FL % Inhibition (10 uM) |
|---|---|---|---|---|
| 19 | 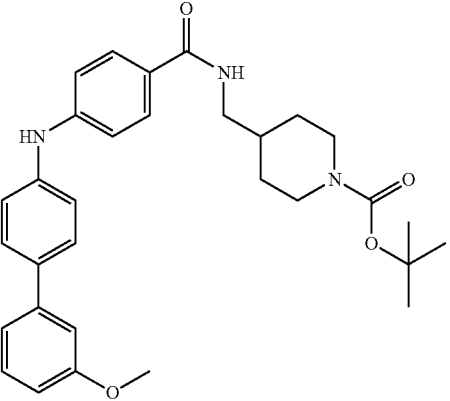 [SMILES: COc1cccc(-c2ccc(Nc3ccc(C(=O)NCC4CCN(C(=O)OC(C)(C)C)CC4)cc3)cc2)c1] | | | 33 |
| 20 | 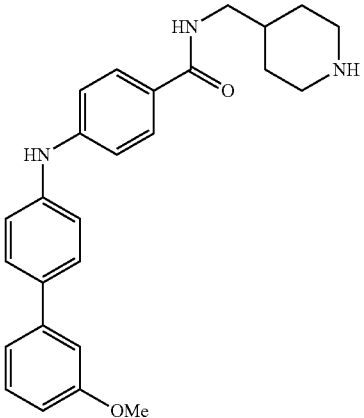 [SMILES: COc1cccc(-c2ccc(Nc3ccc(C(=O)NCC4CCNCC4)cc3)cc2)c1] | | | 1426 |
| 21 | 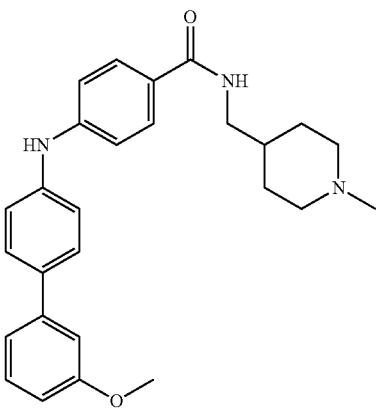 [SMILES: COc1cccc(-c2ccc(Nc3ccc(C(=O)NCC4CCN(C)CC4)cc3)cc2)c1] | | | 1583 |

TABLE 1-continued

SPR, BRET and Cell Viability

| Example No. | Chemical Structure | SPR | Viability data IC$^{50}$(DLD-1) 72 h | BRET RASG12D/CRAF FL % Inhibition (10 uM) |
|---|---|---|---|---|
| 22 | 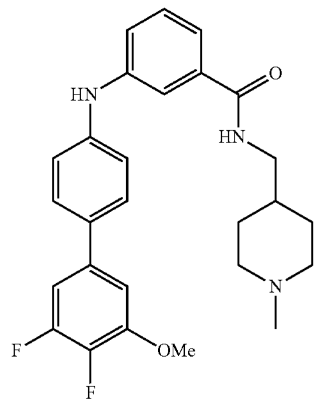 [SMILES: COc1cc(-c2ccc(Nc3cccc(C(=O)NCC4CCN(C)CC4)c3)cc2)cc(F)c1F] | | 1636 | |
| 23 | 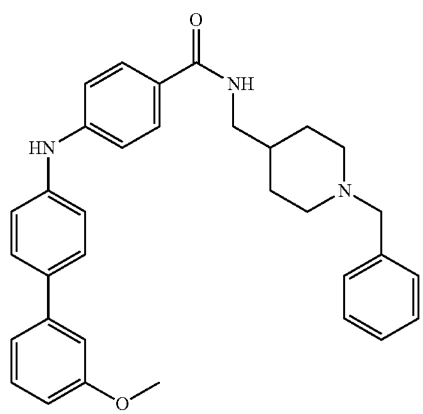 [SMILES: COc1cccc(-c2ccc(Nc3ccc(C(=O)NCC4CCN(Cc5ccccc5)CC4)cc3)cc2)c1] | | 99 | |

Cell Viability DLD-1

The survival of DLD-1 cells was determined over 72 hour periods using the protocol above and a dose response (5, 10, 15, 20 µM) (FIG. 1), allowing a calculation IC50s for each compound (Table 1).

The previously characterized, low RAS affinity compound designated Abd-2 does not affect DLD-1 viability over the range of concentrations nor does the compound designated PPIN-2 compound.

Conversely, the intracellular antibody derived compound designated Abd-7 caused a loss of viability with IC50 of 8.2 µM at 72 hours.

The potency of Examples 1, 2 and 3 of the invention is improved relative to Abd-7, as these compounds show IC50 at 72 hours of 5.3, 7.2 and 4.5 µM respectively (Table 1).

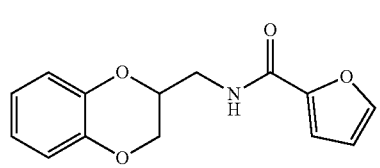

Abd-2 (Reference)

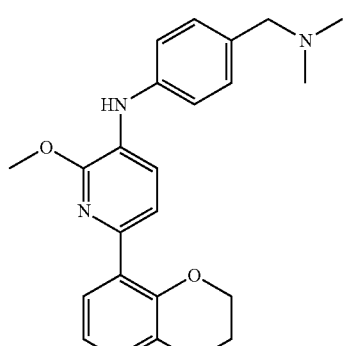

Abd-7 (Reference)

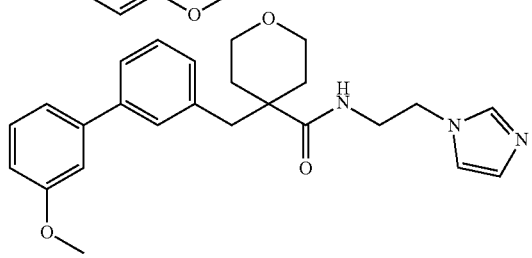

PPIN-2 (Reference)

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

REFERENCES

Vetter I R, Wittinghofer A (2001) The guanine nucleotide-binding switch in three dimensions. Science 294: 1299-1304;

Downward J (2003) Targeting RAS signalling pathways in cancer therapy. Nat Rev Cancer 3: 11-22;

Marshall C J (1995) Specificity of receptor tyrosine kinase signalling: transient versus sustained extracellular signal-regulated kinase activation. Cell 80: 179-185;

Kolch W (2005) Coordinating ERK/MAPK signalling through scaffolds and inhibitors. Nat Rev Mol Cell Biol 6: 827-837;

GonzaleGarcia A, Pritchard C A, Paterson H F, Mavria G, Stamp G, Marshall C J (2005) RalGDS is required for tumor formation in a model of skin carcinogenesis. Cancer Cell 7: 219-226;

Rangarajan A, Hong S J, Gifford A, Weinberg R A (2004) Species- and cell type-specific requirements for cellular transformation. Cancer Cell 6: 171-183;

Adjei A A (2001) Blocking oncogenic Ras signalling for cancer therapy. J Natl Cancer Inst 93: 1062-1074;

Mendelsohn J, Baselga J (2000) The EGF receptor family as targets for cancer therapy. Oncogene 19: 6550-6565;

Johnson L, Mercer K, Greenbaum D, Bronson R T, Crowley D, Tuveson D A, Jacks T (2001) Somatic activation of the K-ras oncogene causes early onset lung cancer in mice. Nature 410: 1111-1116;

Chin L, Tam A, Pomerantz J, Wong M, Holash J, Bardeesy N, Shen Q, O'Hagan R, Pantginis J, Zhou H, Horner II J W, Cordon-Cardo C, Yancopoulos G D, DePinho R A (1999) Essential role for oncogenic Ras in tumour maintenance. Nature 400: 468-472;

Fisher G H, Wellen S L, Klimstra D, Lenczowski J M, Tichelaar J W, Lizak M J, Whitsett J A, Koretsky A, Varmus H E (2001) Induction and apoptotic regression of lung adenocarcinomas by regulation of a K-Ras transgene in the presence and absence of tumor suppressor genes. Genes Dev 15: 3249-3262;

Friday B B, Adjei A A (2005) K-ras as a target for cancer therapy. Biochim Biophys Acta 1756: 127-144;

Cattaneo A, Biocca S (1997) Intracellular Antibodies: Development and Applications. Springer: New York, USA;

Visintin M, Tse E, Axelson H, Rabbitts T H, Cattaneo A (1999) Selection of antibodies for intracellular function using a two-hybrid in vivo system. Proc Natl Acad Sci USA 96:11723-11728

Tse E, Lobato M N, Forster A, Tanaka T, Chung G T Y, Rabbitts T H (2002) Intracellular antibody capture technology: application to selection of single chain Fv recognising the BCR-ABL oncogenic protein. J Mol Biol 317: 85-94;

Tanaka T, Rabbitts T H (2003) Intrabodies based on intracellular capture frameworks that bind the RAS protein with high affinity and impair oncogenic transformation. EMBO J., 22: 1025-1035;

Tanaka T, Lobato M N, Rabbitts T H (2003) Single domain intracellular antibodies: a minimal fragment for direct in vivo selection of antigen-specific intrabodies. J Mol Biol., 331: 1109-1120;

Tanaka et al, (2007) Tumour prevention by a single antibody domain targeting the interaction of signal transduction proteins with RAS; EMBO J., 26, 3250-3259

Blundell T L, Sibanda B L, Montalvao R W, Brewerton S, Chelliah V, Worth C L, Harmer N J, Davies O, Burke D (2006) Structural biology and bioinformatics in drug design: opportunities and challenges for target identification and lead discovery. Philos Trans R Soc Lond B Biol Sci 361: 413-423

The invention claimed is:

1. A compound of Formula Ih, Ii, Ij or Ik, or a salt or solvate thereof:

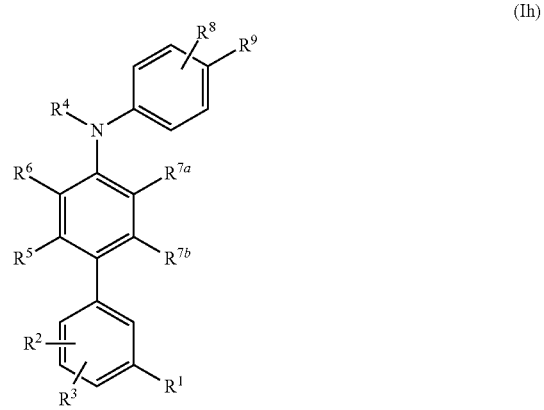

(Ih)

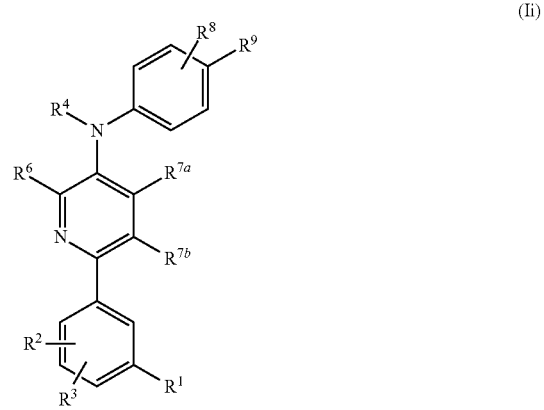

(Ii)

-continued

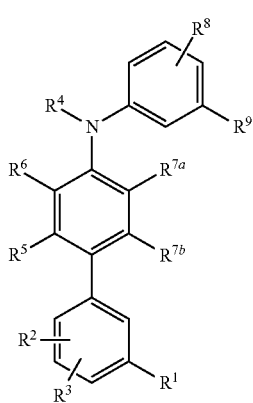
(Ij)

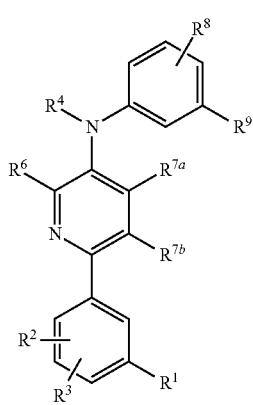
(Ik)

wherein,
R¹ is selected from $C_{1-6}$ alkoxy and $NR^pR^q$, wherein $R^p$ and $R^q$ are independently selected from hydrogen, $C_{1-6}$ alkyl and $C(O)C_{1-3}$alkyl;
$R^2$ and $R^3$ are independently selected from the group consisting of hydrogen, hydroxyl, halogen, CN, $C_{1-6}$ haloalkyl, $C_{1-6}$ haloalkoxy, $O-C_{1-6}$ alkyl and $C_{1-6}$ alkyl;
$R^4$ is selected from hydrogen and $C_{1-3}$ alkyl;
$R^5$ is selected from the group consisting of hydrogen, hydroxyl, =O, halogen, CN, $C_{1-6}$ haloalkyl, $C_{1-6}$ haloalkoxy, $O-C_{1-6}$ alkyl, $C_{1-6}$ alkyl and $NR^pR^q$;
$R^6$ is selected from the group consisting of hydrogen, hydroxyl, halogen, $C_{1-6}$ haloalkyl, $C_{1-6}$ haloalkoxy, $O-C_{1-6}$ alkyl, $C_{1-6}$ alkyl and $NR^pR^q$;
$R^{7a}$ and $R^{7b}$ are independently selected from hydrogen, hydroxyl, halogen, $C_{1-6}$ haloalkyl, $C_{1-6}$ haloalkoxy, $O-C_{1-6}$ alkyl and $C_{1-6}$ alkyl;
$R^8$ is selected from selected from the group consisting of hydrogen and $C_{1-6}$ alkyl; and
$R^9$ is selected from $C_{1-6}$ alkyl, optionally substituted with one or more groups of HNMe or $NMe_2$; or
$R^9$ is $-(CH_2)_{1-6}$-heterocycle, wherein said heterocycle is or morpholine optionally substituted with one or more $C_{1-6}$ alkyl; or
$R^9$ if $-C(O)NH(CH_2)_{1-4}$-heterocycle, wherein said heterocycle is piperidine substituted by $R^k$; wherein $R^k$ is selected from the group consisting of hydrogen, $C_{1-6}$ alkyl optionally substituted with phenyl, $-C(O)OH$, and $-C(O)OC_{1-6}$ alkyl.

2. The compound according to formula Ih, Ii, Ij or Ik, or a salt or solvate thereof, according to claim 1 wherein R¹ is selected from $C_{1-3}$ alkoxy and $NR^pR^q$.

3. The compound according to formula Ih, Ii, Ij or Ik, or a salt or solvate thereof, according to claim 1 wherein $R^2$ and $R^3$ are independently selected from hydrogen, halogen and $C_{1-6}$ alkyl.

4. The compound according to formula Ih, Ii, Ij or Ik, or a salt or solvate thereof, according to claim 1 wherein $R^5$ is selected from hydrogen and halogen.

5. The compound according to formula Ih, Ii, Ij or Ik, or a salt or solvate thereof, according to claim 1 wherein $R^6$ is selected from hydrogen, halogen and $O-C_{1-3}$ alkyl.

6. The compound according to formula Ih, Ii, Ij or Ik, or a salt or solvate thereof, according to claim 1 wherein $R^{7a}$ and $R^{7b}$ are both hydrogen.

7. The compound according to formula Ih, Ii, Ij or Ik, or a salt or solvate thereof, according to claim 1 wherein $R^4$ is selected from hydrogen or methyl.

8. The compound according to formula Ih, Ii, Ij or Ik, or a salt or solvate thereof, according to claim 1 wherein $R^9$ is $C_{1-6}$ alkyl substituted with $NMe_2$.

9. A compound, or a salt or solvate thereof, selected from the group consisting of:
N-(4-((dimethylamino)methyl)phenyl)-3'-methoxy-[1,1'-biphenyl]-4-amine;
N-(4-((dimethylamino)methyl)phenyl)-3,3'-dimethoxy-[1,1'-biphenyl]-4-amine;
N-(4-((dimethylamino)methyl)phenyl)-2-fluoro-3,3'-dimethoxy-[1,1'-biphenyl]-4-amine;
N-(4-((dimethylamino)methyl)phenyl)-4'-fluoro-3'-methoxy-[1,1'-biphenyl]-4-amine;
N-(4-((dimethylamino)methyl)phenyl)-3',4'-difluoro-5'-methoxy-[1,1'-biphenyl]-4-amine;
N-(4-((dimethylamino)methyl)phenyl)-3'-fluoro-5'-methoxy-[1,1'-biphenyl]-4-amine;
N-(4-((dimethylamino)methyl)phenyl)-3'-methoxy-5'-methyl-[1,1'-biphenyl]-4-amine;
N-(3,5-dimethylphenyl)-2-fluoro-3,3'-dimethoxy-[1,1'-biphenyl]-4-amine;
N-(3,5-dimethylphenyl)-3'-methoxy-[1,1'-biphenyl]-4-amine;
N-(5-((dimethylamino)methyl)-2-methylphenyl)-3'-methoxy-[1,1'-biphenyl]-4-amine;
N-(3-((2,6-dimethylmorpholino)methyl)phenyl)-3'-methoxy-[1,1'-biphenyl]-4-amine;
N-(4-((2,6-dimethylmorpholino)methyl)phenyl)-3'-methoxy-[1,1'-biphenyl]-4-amine;
N-(4-((dimethylamino)methyl)phenyl)-2-methoxy-6-(3-methoxyphenyl)pyridin-3-amine;
N-(3-((dimethylamino)methyl)phenyl)-2-methoxy-6-(3-methoxyphenyl)pyridin-3-amine;
N-(4-((dimethylamino)methyl)phenyl)-6-(3-methoxyphenyl)pyridin-3-amine;
3-((3'-methoxy-[1,1'-biphenyl]-4-yl)amino)-N-(piperidin-4-ylmethyl)benzamide;
N-(4-((dimethylamino)methyl)phenyl)-3'-methoxy-4'-methyl-[1,1'-biphenyl]-4-amine;
4-((3'-methoxy-[1,1'-biphenyl]-4-yl)amino)-N-(piperidin-4-ylmethyl)benzamide;
N-((1-benzylpiperidin-4-yl)methyl)-4-((3'-methoxy-[1,1'-biphenyl]-4-yl)amino)benzamide;
4-((3'-methoxy-[1,1'-biphenyl]-4-yl)amino)-N-((1-methylpiperidin-4-yl)methyl)benzamide; and
4-((3',4'-difluoro-5'-methoxy-[1,1'-biphenyl]-4-yl)amino)-N-((1-methylpiperidin-4-yl)methyl)benzamide.

10. A pharmaceutical composition comprising a compound according to claim 1 and a pharmaceutically acceptable salt or solvate thereof, and one or more pharmaceutically acceptable excipients.

* * * * *